United States Patent
Lisogurski et al.

(10) Patent No.: US 8,886,294 B2
(45) Date of Patent: Nov. 11, 2014

(54) METHODS AND SYSTEMS FOR PHOTOACOUSTIC MONITORING USING INDICATOR DILUTION

(75) Inventors: Daniel Lisogurski, Boulder, CO (US); Youzhi Li, Longmont, CO (US); Bo Chen, Louisville, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/308,086

(22) Filed: Nov. 30, 2011

(65) Prior Publication Data

US 2013/0137959 A1    May 30, 2013

(51) Int. Cl.
| | |
|---|---|
| A61B 5/05 | (2006.01) |
| A61B 5/026 | (2006.01) |
| A61B 5/0275 | (2006.01) |
| A61B 5/029 | (2006.01) |
| A61B 5/00 | (2006.01) |
| A61B 5/1455 | (2006.01) |

(52) U.S. Cl.
CPC ............ *A61B 5/0261* (2013.01); *A61B 5/0275* (2013.01); *A61B 5/2416* (2013.01); *A61B 5/6867* (2013.01); *A61B 5/1455* (2013.01); *A61B 5/029* (2013.01); *A61B 5/0095* (2013.01)
USPC ........... 600/473; 600/340; 600/476; 600/465; 600/480

(58) Field of Classification Search
CPC ............... A61B 5/0261; A61B 5/0275; A61B 5/02416; A61B 5/029; A61B 5/1455
USPC ........................ 600/473, 480, 465, 526, 342
See application file for complete search history.

(56) References Cited

U.S. PATENT DOCUMENTS

| | | | |
|---|---|---|---|
| 4,385,634 A | 5/1983 | Bowen | |
| 4,874,949 A | 10/1989 | Harris et al. | |
| 5,348,002 A | 9/1994 | Caro | |
| 5,595,182 A * | 1/1997 | Krivitski | 600/505 |
| 5,657,754 A | 8/1997 | Rosencwaig | |
| 5,840,023 A | 11/1998 | Oraevsky et al. | |
| 5,941,821 A | 8/1999 | Chou | |

(Continued)

FOREIGN PATENT DOCUMENTS

| | | |
|---|---|---|
| EP | 0282234 | 9/1988 |
| JP | 2007259918 | 10/2007 |

(Continued)

OTHER PUBLICATIONS

Brecht, H., "Noninvasive Optoacoustic Monitoring of Blood Oxygenation in Large Blood Vessels," Thesis., The University of Texas Medical Branch, Dec. 2007.

(Continued)

*Primary Examiner* — Long V. Le
*Assistant Examiner* — Helene Bor
(74) *Attorney, Agent, or Firm* — Fletcher Yoder PC

(57) ABSTRACT

A patient monitoring system may provide photoacoustic sensing based on an indicator dilution to determine one or more physiological parameters of a subject. The system may detect an acoustic pressure signal, which may include one or more thermo-dilution responses, one or more hemo-dilution responses, or a combination thereof, using one or more sensor units. The system may use multiple light sources and/or detectors to diagnose and/or improve signal to noise ratio, distinguish between arterial and venous signals, prevent under-sampling, and separate the effects of hemo-dilution and thermo-dilution.

21 Claims, 7 Drawing Sheets

(56) References Cited

U.S. PATENT DOCUMENTS

| | | | |
|---|---|---|---|
| 6,049,728 A | 4/2000 | Chou | |
| 6,104,942 A | 8/2000 | Kruger | |
| 6,299,583 B1 * | 10/2001 | Eggers et al. | 600/526 |
| 6,309,352 B1 | 10/2001 | Oraevsky et al. | |
| 6,403,944 B1 | 6/2002 | MacKenzie et al. | |
| 6,405,069 B1 | 6/2002 | Oraevsky et al. | |
| 6,466,806 B1 | 10/2002 | Geva et al. | |
| 6,484,004 B1 | 11/2002 | Schein et al. | |
| 6,498,942 B1 | 12/2002 | Esenaliev et al. | |
| 6,751,490 B2 | 6/2004 | Esenaliev et al. | |
| 6,757,554 B2 * | 6/2004 | Rubinstein et al. | 600/317 |
| 6,839,496 B1 | 1/2005 | Mills et al. | |
| 6,846,288 B2 | 1/2005 | Nagar et al. | |
| 7,322,972 B2 | 1/2008 | Viator et al. | |
| 7,430,445 B2 | 9/2008 | Esenaliev et al. | |
| 7,515,948 B1 | 4/2009 | Balberg et al. | |
| 7,729,734 B2 | 6/2010 | Mandelis et al. | |
| 2002/0172323 A1 * | 11/2002 | Karellas et al. | 378/51 |
| 2003/0216663 A1 * | 11/2003 | Jersey-Willuhn et al. | 600/547 |
| 2004/0039379 A1 | 2/2004 | Viator et al. | |
| 2006/0184042 A1 | 8/2006 | Wang et al. | |
| 2006/0189926 A1 | 8/2006 | Hall et al. | |
| 2006/0224053 A1 * | 10/2006 | Black et al. | 600/310 |
| 2006/0253043 A1 | 11/2006 | Zhang et al. | |
| 2006/0272418 A1 | 12/2006 | Maris et al. | |
| 2007/0059247 A1 | 3/2007 | Lindner et al. | |
| 2007/0197886 A1 | 8/2007 | Naganuma et al. | |
| 2007/0239003 A1 | 10/2007 | Shertukde et al. | |
| 2008/0015434 A1 | 1/2008 | Rubinstein et al. | |
| 2008/0255433 A1 | 10/2008 | Prough et al. | |
| 2010/0016731 A1 | 1/2010 | Eggers et al. | |
| 2010/0094144 A1 | 4/2010 | Doron | |
| 2010/0152559 A1 | 6/2010 | Cheng et al. | |
| 2010/0285518 A1 | 11/2010 | Viator et al. | |
| 2010/0292547 A1 | 11/2010 | Mandelis et al. | |
| 2010/0298689 A1 * | 11/2010 | Wang | 600/407 |
| 2011/0071373 A1 | 3/2011 | Li et al. | |
| 2011/0201914 A1 | 8/2011 | Wang et al. | |
| 2011/0275890 A1 | 11/2011 | Wang et al. | |
| 2012/0029829 A1 | 2/2012 | Li et al. | |
| 2012/0197117 A1 | 8/2012 | Picot et al. | |
| 2013/0137960 A1 | 5/2013 | Lisogurski et al. | |
| 2013/0144147 A1 | 6/2013 | Li et al. | |
| 2013/0144148 A1 | 6/2013 | Li et al. | |

FOREIGN PATENT DOCUMENTS

| | | | |
|---|---|---|---|
| RU | 2238108 C1 | | 10/2004 |
| WO | 080/00530 A1 | * | 4/1980 |
| WO | 9612440 A1 | | 5/1996 |
| WO | WO 03048704 A1 | * | 6/2003 |

OTHER PUBLICATIONS

Esenaliev, R. O. et al., "Continuous, noninvasive monitoring of total hemoglobin concentration by an optoacoustic technique," Applied Optics, vol. 43, No. 17, pp. 3401-3407, 2007.

Guo, Z. et al., "Calibration-free absolute quantification of optical absorption coefficients using acoustic spectra in 3D photoacoustic microscopy of biological tissue," Optics Letters, vol. 35, No. 12, pp. 2067-2069, 2010.

Hu, S. et al., "Noninvasive label-free imaging of microhemodynamics by optical-respolution photoacustic microscopy," Optics Express, vol. 17, No. 9, pp. 7688-7694, 2009.

Petrova, I. Y. et al., "Clinical tests of highly portable, 2-lb, laser diode-based, noninvasive, optoacoustic hemoglobin monitor," Procedings of SPIE, vol. 7177, 717705, 2009.

Pramanik, M. et al., "Thermoacoustic and photoacoustic sensing of temperature," Journal of Biomedical Optics, vol. 14(5), 054024, 2009.

Ranasinghesagara, J. C. et al., "Combined photoacoustic and oblique-incidence diffuse reflectance system for quantitative photoacoustic imaging in turbid media," Journal of Biomedical Optics, vol. 15, 046016, 2010.

Telenkov, S. A. et al., "Photothermoacoustic imaging of biological tissues: maximum depth characterization comparison of time and frequency-domain measurements," Journal of Biomedical Optics, vol. 14(4), 044025, 2009.

Van Bortel, L.M. et al., "Influence of aging on arterial compliance," Journal of Human Hypertension, vol. 12, pp. 583-586, 1998.

Kaushal, P. et al., "Inter-relations among declines in arterial distensibility, baroreflex function and respiratory sinus arrhythmia," Journal of the American College of Cardiology, vol. 39, No. 9, pp. 1524-1530, 2002.

International Search Report and Written Opinion of the International Searching Authority for application No. PCT/US 2012/067129, mailed on Feb. 28, 2013.

Grodins, Fred S., et al.; "Basic concepts in the determination of vascular volumes by indicator-dilution methods," Circ. Res. vol. 10, 1962, pp. 429-446.

Elings, V.B., et al.; "Indicator dilution using fluorescent indicator," Journal of Applied Physiology, May 1, 1982, vol. 52, No. 5, pp. 1368-1374.

Krivitski, Nikolai M., et al.; Volume of extravascular lung fluid determined by blood ultrasound velocity and electrical impedance dilution, ASAIO Journal, vol. 44, No. 5, 1998, pp. M535-M540.

Wintermark, M., et al.; "Quantitative assessment of regional cerebral blood flows by perfusion CT studies at low injection rates," Eur. Radiol. vol. 11, 2001, pp. 1220-1230.

Garland, Jocelyn S., et al.; "Measurement of extravascular lung water in hemodialysis patients using blood ultrasound velocity and optical density dilution," ASAIO Journal, vol. 48, 2002, pp. 398-403.

Fang, Ying et al.; "Laser Photothermoacoustic Heterodyned Lock-in Depth Profilometry in Turbid Tissue Phantoms," Physc. Rev. E, vol. 72, 2005, pp. 051908-1-051908-11.

Larina, Irina V., et al.; "Real-Time Optoacoustic Monitoring of Temperature in Tissues," J. Phys. D: Appl. Phys., vol. 38, 2005, pp. 2633-2639.

Laufer, Jan, et al.; "In Vitro measurements of absolute blood oxygen saturation using pulsed near-infrared photoacoustic spectroscopy: Accuracy and Resolution," Phys. Med. Biol. vol. 50, 2005, pp. 4409-4428.

Isakow, Warran et al.; "Extravascular lung water measurements and hemodynamic monitoring in the critically ill," Am. J. Physiol. Lung Cell Mol. Physiol., vol. 291, 2006, pp. L1118-L1131.

Fernandez-Mondejar, Enrique, et al.; "How important is the measurement of extravascular lung water?" Curr. Opin. Cirt. Care, vol. 13, 2007, pp. 79-83.

Effros, Richard M., et al.; "Indicator dilution measurements of extravascular lung water: Basic assumptions and observations," 2008, vol. 294, pp. L1023-L1031.

Guo, Zijian, et al.; "On the Speckle-free nature of photoacoustic tomography," Med. Phys., vol. 37, No. 9, 2009, pp. 4084-4088.

Reuter, Daniel A., et al.; "Cardiac output monitoring using indicator-dilution techniques," Anesthesia and Analgesia, vol. 110, No. 3, 2010, pp. 799-811.

International Search Report for Application No. PCT/US2012/067125 mailed Feb. 28, 2013.

International Preliminary Report on Patentability for PCT Application No. PCT/US2012/067770 dated Jun. 19, 2014; 5 pgs.

* cited by examiner

METHODS AND SYSTEMS FOR PHOTOACOUSTIC MONITORING USING INDICATOR DILUTION

The present disclosure relates to monitoring physiological parameters, and more particularly relates to monitoring physiological parameters using an indicator dilution and photoacoustic analysis.

SUMMARY

A physiological monitoring system may be configured to determine a physiological parameter of a subject, using photoacoustic analysis and an indicator dilution response. The system may include one or more light sources that may provide one or more photonic signals to one or more blood vessel sites of the subject. The system may also include one or more acoustic detectors that may detect acoustic pressure signal(s) from the one or more blood vessel site, caused by the absorption of at least some of the photonic signal by one or more constituents at the first blood vessel site.

In some embodiments, the system may detect a first acoustic pressure signal from a first blood vessel site using a first acoustic detector. The first acoustic pressure signal may be caused by absorption of at least some of a photonic signal provided to the first blood vessel site by one or more constituents at the first blood vessel site. The first acoustic pressure signal may include a dilution response corresponding to an indicator. The system may also detect a second acoustic pressure signal from a second blood vessel site using a second acoustic detector. The second acoustic pressure signal may be caused by absorption of at least some of a photonic signal provided to the second blood vessel site by one or more constituents at the second blood vessel site. The second acoustic pressure signal may include a dilution response corresponding to the same indicator. The system may determine a physiological parameter based at least in part on a first photoacoustic signal derived from the first acoustic pressure signal and based at least in part on a second photoacoustic signal derived from the second acoustic pressure signal. The physiological parameter may include cardiac output, intrathoracic blood volume, intrathoracic circulatory volume, global end-diastolic volume, pulmonary circulatory volume, and/or extravascular lung water. In some embodiments, the first blood vessel site and the second blood vessel site may be located at substantially the same blood vessel site, and the corresponding photoacoustic signals, and/or physiological parameters derived thereof, may be averaged. In some embodiments, the second blood vessel site is located distal to the first blood vessel site in the same blood vessel of the subject. In some embodiments, the first and second blood vessel sites are respective sites of a right blood vessel and a corresponding left blood vessel of the subject. In some embodiments, the first acoustic pressure signal may include a first response to a first indicator and a second response to a second indicator. The second acoustic pressure signal may include a first response to the first indicator and a second response to the second indicator. The first and the second indicators may be introduced to the subject at different temperatures. In some embodiments, the system may determine a signal confidence such as, for example, signal to noise ratio, based on at least one of the first acoustic pressure signal and the second acoustic pressure signal. The system may determine a physiological parameter based on the determined signal confidence.

In some embodiments, the system may use one or more acoustic detectors to detect one or more acoustic pressure signals resulting from a photoacoustic response to one or more photonic signals at a monitoring site. The monitoring site may include one or more blood vessel sites. The one or more acoustic pressure signals may include a first indicator dilution response corresponding to an indicator passing through a first blood vessel site and a second indicator dilution response corresponding to the indicator passing through a second blood vessel site. In some embodiments, the system may analyze the first indicator dilution response and the second indicator dilution response. The system may determine a physiological parameter based at least in part on the analysis and based at least in part on at least one of the first indicator dilution response and the second indicator dilution response. The analysis may include, for example, determining a time difference between the first indicator dilution response and the second indicator dilution response, determine a shape difference between the first indicator dilution response and the second indicator dilution response, any other analytical step, or any combination thereof. The system may determine the physiological parameter based at least in part on the first indicator dilution response and based at least in part on the second indicator dilution response. The physiological parameter may include cardiac output, intrathoracic blood volume, intrathoracic circulatory volume, global end-diastolic volume, pulmonary circulatory volume, and/or extravascular lung water. In some embodiments, the first blood vessel site may be an arterial site (e.g., in a carotid artery, a radial artery, and/or ulnar artery), and the second blood vessel site may be a venous site (e.g., a jugular vein, a cephalic vein, and/or an ulnar vein. In some embodiments, the system may distinguish the first indicator dilution response from the second indicator dilution response, and determine the physiological parameter based on the first indicator dilution response or the second indicator dilution response.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
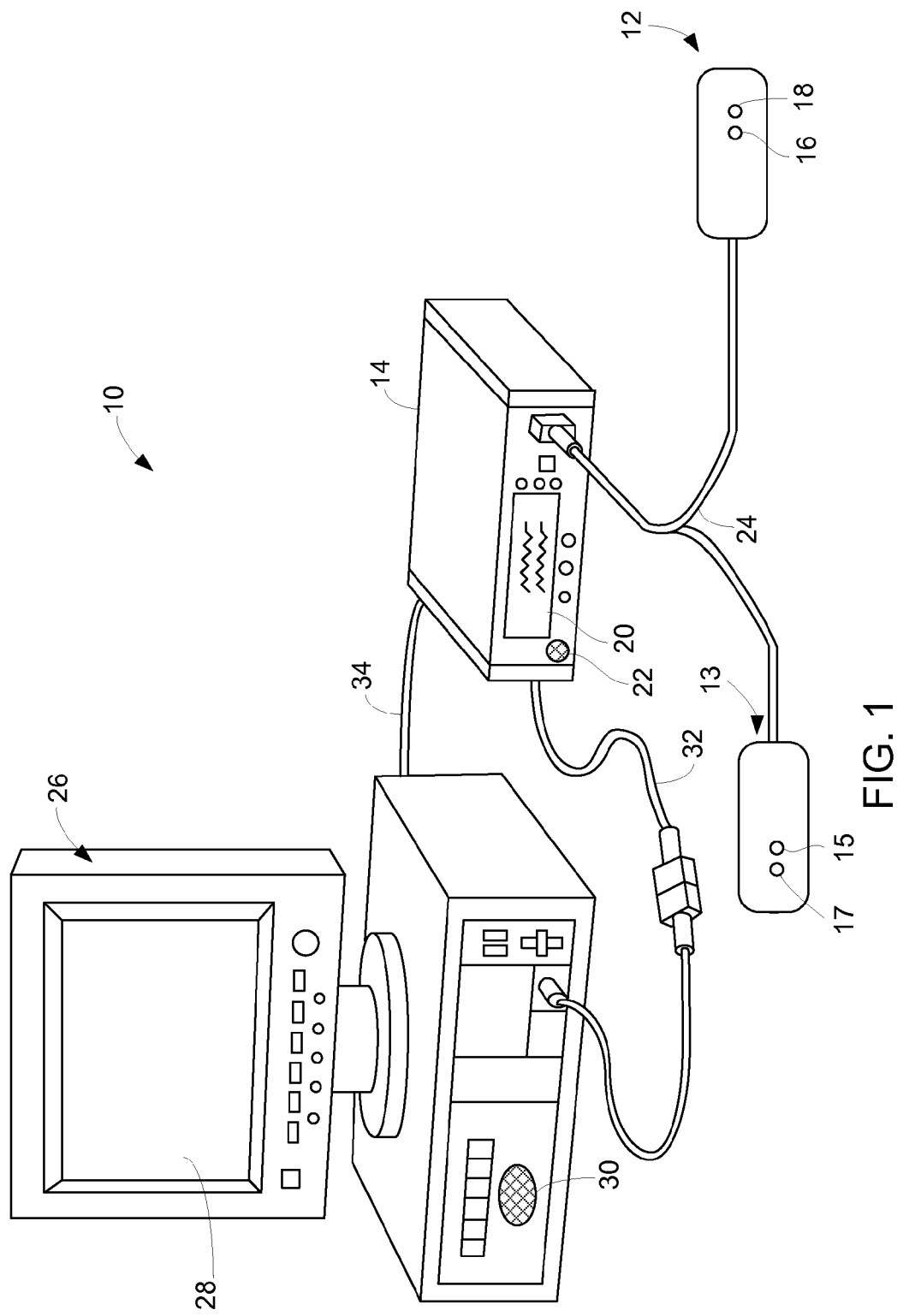
FIG. 1 shows an illustrative physiological monitoring system, in accordance with some embodiments of the present disclosure.

Photoacoustics (or "optoacoustics") or the photoacoustic effect (or "optoacoustic effect") refers to the phenomenon in which one or more wavelengths of light are presented to and absorbed by one or more constituents of an object, thereby causing an increase in kinetic energy of the one or more constituents, which causes an associated pressure response within the object. Particular modulations or pulsing of the incident light, along with measurements of the corresponding pressure response in, for example, tissue of the subject, may be used for medical imaging, physiological parameter determination, or both. For example, the concentration of a constituent, such as hemoglobin (e.g., oxygenated, deoxygenated and/or total hemoglobin) may be determined using photoacoustic analysis. In a further example, one or more hemodynamic parameters such as cardiac output, intrathoracic blood volume, intrathoracic circulatory volume, global end-diastolic volume, pulmonary circulatory volume, extravascular lung water, and/or any other suitable hemodynamic parameters may be determined using photoacoustic analysis and indicator dilution techniques.

A photoacoustic system may include one or more photoacoustic sensors that are placed at a site on a subject, typically the wrist, palm, neck, forehead, temple, or anywhere an artery or vessel is accessible noninvasively. In some embodiments, the photoacoustic techniques described herein are used to monitor large blood vessels, such as a major artery or vein which may be near the heart (e.g., the carotid or radial arteries or the jugular vein). The photoacoustic system may use a light source, and any suitable light guides (e.g., fiber optics), to pass light through the subject's tissue, or a combination of tissue thereof (e.g., organs), and an acoustic detector to sense the pressure response of the tissue induced by the light absorption by a blood vessel. Tissue may include muscle, fat, blood, blood vessels, and/or any other suitable tissue types. In some embodiments, the light source may be a laser or laser diode, operated in pulsed or continuous wave (CW) mode. In some embodiments, the acoustic detector may be an ultrasound detector, which may be suitable to detect pressure fluctuations arising from the constituent's absorption of the incident light of the light source.

In some embodiments, the light from the light source may be focused, shaped, or otherwise spatially modulated to illuminate a particular region of interest. In some arrangements, photoacoustic monitoring may allow relatively higher spatial resolution than line of sight optical techniques (e.g., path integrated absorption measurements). The enhanced spatial resolution of the photoacoustic technique may allow for imaging, scalar field mapping, and other spatially resolved results, in 1, 2, or 3 spatial dimensions. The acoustic response to the photonic excitation may radiate from the illuminated region of interest, and accordingly may be detected at multiple positions.

The photoacoustic system may measure the pressure response that is received at the acoustic sensor as a function of time. The photoacoustic system may also include sensors at multiple locations. A signal representing pressure versus time or a mathematical manipulation of this signal (e.g., a scaled version thereof, etc.) may be referred to as the photoacoustic (PA) signal. The PA signal may be derived from a detected acoustic pressure signal by selecting a suitable subset of points of an acoustic pressure signal. The PA signal may be used to calculate any of a number of physiological parameters, including a concentration of a blood constituent (e.g., hemoglobin), at a particular spatial location. In some embodiments, PA signals from multiple spatial locations may be used to construct an image (e.g., imaging blood vessels) or a scalar field (e.g., a hemoglobin concentration field).

In some applications, the light passed through the tissue is selected to be of one or more wavelengths that are absorbed by the constituent in an amount representative of the amount of the constituent present in the tissue. The absorption of light passed through the tissue varies in accordance with the amount of the constituent in the tissue. For example, Red and/or infrared (IR) wavelengths may be used because highly oxygenated blood will absorb relatively less Red light and more IR light than blood with a lower oxygen saturation.

Any suitable light source may be used, and characteristics of the light provided by the light source may be controlled in any suitable manner. In some embodiments, a pulsed light source may be used to provide relatively short-duration pulses (e.g., nanosecond pulses) of light to the region of interest. Accordingly, the use of a pulse light source may result in a relatively broadband acoustic response (e.g., depending on the pulse duration). The use of a pulsed light source will be referred to herein as the "Time Domain Photoacoustic" (TD-PA) technique. A convenient starting point for analyzing a TD-PA signal is given by Eq. 1:

$$p(z) = \Gamma \mu_a \phi(z) \tag{1}$$

under conditions where the irradiation time is small compared to the characteristic thermal diffusion time determined by the properties of the specific tissue type. Referring to Eq. 1, p(z) is the PA signal (indicative of the maximum induced pressure rise, derived from an acoustic pressure signal) at spatial location z indicative of acoustic pressure, $\Gamma$ is the dimensionless Grüneisen parameter of the tissue, $\mu_a$ is the effective absorption coefficient of the tissue (or constituent thereof) to the incident light, and $\phi(z)$ is the optical fluence at spatial location z. The Grüneisen parameter is a dimensionless description of thermoelastic effects, and may be illustratively formulated by Eq. 2:

$$\Gamma = \frac{\beta c_a^2}{C_P} \tag{2}$$

where $c_a$ is the speed of sound in the tissue, $\beta$ is the isobaric volume thermal expansion coefficient, and $C_P$ is the specific heat at constant pressure. In some circumstances, the optical fluence, at spatial location z (within the subject's tissue) of interest may be dependent upon the light source, the location itself (e.g., the depth), and optical properties (e.g., scattering coefficient, absorption coefficient, or other properties) along the optical path. For example, Eq. 3 provides an illustrative expression for the attenuated optical fluence at a depth z:

$$\phi(z) = \phi_0 e^{-\mu_{eff} z} \tag{3}$$

where $\phi_0$ is the optical fluence from the light source incident at the tissue surface, z is the path length (i.e., the depth into the tissue in this example), and $\mu_{eff}$ is an effective attenuation coefficient of the tissue along the path length in the tissue in this example.

In some embodiments, a more detailed expression or model may be used rather than the illustrative expression of Eq. 3. In some embodiments, the actual pressure encountered by an acoustic detector may be proportional to Eq. 1, as the focal distance and solid angle (e.g., face area) of the detector may affect the actual measured PA signal. In some embodiments, an ultrasound detector positioned relatively farther away from the region of interest, will encounter a relatively smaller acoustic pressure. For example, the acoustic pressure received at a circular area $A_d$ positioned at a distance R from the illuminated region of interest may be given by Eq. 4:

$$p_d = p(z) f(r_s, R, A_d) \quad (4)$$

where $r_s$ is the radius of the illuminated region of interest (and typically $r_s < R$), and p(z) is given by Eq. 1. In some embodiments, the detected acoustic pressure amplitude may decrease as the distance R increases (e.g., for a spherical acoustic wave).

In some embodiments, a modulated CW light source may be used to provide a photonic excitation of a tissue constituent to cause a photoacoustic response in the tissue. The CW light source may be intensity modulated at one or more characteristic frequencies. The use of a CW light source, intensity modulated at one or more frequencies, will be referred to herein as the "Frequency Domain Photoacoustic" (FD-PA) technique. Although the FD-PA technique may include using frequency domain analysis, the technique may use time domain analysis, wavelet domain analysis, or any other suitable analysis, or any combination thereof. Accordingly, the term "frequency domain" as used in "FD-PA" refers to the frequency modulation of the photonic signal, and not to the type of analysis used to process the photoacoustic response.

Under some conditions, the acoustic pressure p(R,t) at detector position R at time t, may be shown illustratively by Eq. 5:

$$p(R, t) \sim \frac{p_0(r_0, \omega)}{R} e^{-i\omega(t-\tau)} \quad (5)$$

where $r_0$ is the position of the illuminated region of interest, $\omega$ is the angular frequency of the acoustic wave (caused by modulation of the photonic signal at frequency $\omega$), R is the distance between the illuminated region of interest and the detector, and $\tau$ is the travel time delay of the wave equal to $R/c_a$, where $c_a$ is the speed of sound in the tissue. The FD-PA spectrum $p_0(r_0,\omega)$ of acoustic waves is shown illustratively by Eq. 6:

$$p_0(r_0, \omega) = \frac{\Gamma \mu_a \phi(r_0)}{2(\mu_a c_a - i\omega)} \quad (6)$$

where $\mu_a c_a$ represents a characteristic frequency (and corresponding time scale) of the tissue.

In some embodiments, a FD-PA system may temporally vary the characteristic modulation frequency of the CW light source, and accordingly the characteristic frequency of the associated acoustic response. For example, the FD-PA system may use linear frequency modulation (LFM), either increasing or decreasing with time, which is sometimes referred to as "chirp" signal modulation. Shown in Eq. 7 is an illustrative expression for a sinusoidal chirp signal r(t):

$$r(t) = \sin\left(t\left(\omega_0 + \frac{b}{2}t\right)\right) \quad (7)$$

where $\omega_0$ is a starting angular frequency, and b is the angular frequency scan rate. Any suitable range of frequencies (and corresponding angular frequencies) may be used for modulation such as, for example, 1-5 MHz, 200-800 kHz, or other suitable range, in accordance with the present disclosure. In some embodiments, signals having a characteristic frequency that changes as a nonlinear function of time may be used. Any suitable technique, or combination of techniques thereof, may be used to analyze a FD-PA signal. Two such exemplary techniques, a correlation technique and a heterodyne mixing technique, will be discussed below as illustrative examples.

In some embodiments, the correlation technique may be used to determine the travel time delay of the FD-PA signal. In some embodiments, a matched filtering technique may be used to process a PA signal. As shown in Eq. 8:

$$B_s(t-\tau) = \frac{1}{2\pi} \int_{-\infty}^{\infty} H(\omega) S(\omega) e^{i\omega t} d\omega \quad (8)$$

Fourier transforms (and inverse transforms) are used to calculate the filter output $B_s(t-T)$, in which $H(\omega)$ is the filter frequency response, $S(\omega)$ is the Fourier transform of the PA signal s(t), and T is the phase difference between the filter and signal. In some circumstances, the filter output of expression of Eq. 8 may be equivalent to an autocorrelation function. Shown in Eq. 9:

$$S(\omega) = \frac{1}{2\pi} \int_{-\infty}^{\infty} s(t) e^{-i\omega t} dt \quad (9)$$

is an expression for computing the Fourier transform S(w) of the PA signal s(t). Shown in Eq. 10:

$$H(\omega) = S^*(\omega) e^{-i\omega \tau} \quad (10)$$

is an expression for computing the filter frequency response $H(\omega)$ based on the Fourier transform of the PA signal s(t), in which $S^*(\omega)$ is the complex conjugate of $S(\omega)$. It can be observed that the filter frequency response of Eq. 10 requires the frequency character of the PA signal be known beforehand to determine the frequency response of the filter. In some embodiments, as shown by Eq. 11:

$$B(t) = \int_{-\infty}^{\infty} r(t') s(t+t') dt' \quad (11)$$

the known modulation signal r(t) may be used for generating a cross-correlation with the PA signal. The cross-correlation output B(t) of Eq. 11 is expected to exhibit a peak at a time t equal to the acoustic signal travel time $\tau$. Assuming that the temperature response and resulting acoustic response follow the illumination modulation (e.g., are coherent), Eq. 11 may allow calculation of the time delay, depth information, or both.

In some embodiments, the heterodyne mixing technique may be used to determine the travel time delay of the FD-PA signal. The FD-PA signal, as described above, may have similar frequency character as the modulation signal (e.g., coherence), albeit shifted in time due to the travel time of the acoustic signal. For example, a chirp modulation signal, such as r(t) of Eq. 7, may be used to modulate a CW light source. Heterodyne mixing uses the trigonometric identity of the following Eq. 12:

$$\sin(A)\sin(B) = \tfrac{1}{2}[\cos(A-B) - \cos(A+B)] \quad (12)$$

which shows that two signals may be combined by multiplication to give periodic signals at two distinct frequencies (i.e., the sum and the difference of the original frequencies). If the result is passed through a low-pass filter to remove the higher frequency term (i.e., the sum), the resulting filtered, frequency shifted signal may be analyzed. For example, Eq. 13 shows a heterodyne signal L(t):

$$L(t) = \langle r(t)s(t) \rangle \cong \left\langle Kr(t)r\left(t - \frac{R}{c_a}\right)\right\rangle = \frac{1}{2}K\cos\left(\frac{R}{c_a}bt + \theta\right) \quad (13)$$

calculated by low-pass filtering (shown by angle brackets) the product of modulation signal r(t) and PA signal s(t). If the PA signal is assumed to be equivalent to the modulation signal, with a time lag $R/c_a$ due to travel time of the acoustic wave and amplitude scaling K, then a convenient approximation of Eq. 13 may be made, giving the rightmost term of Eq. 13. Analysis of the rightmost expression of Eq. 13 may provide depth information, travel time, or both. For example, a fast Fourier transform (FFT) may be performed on the heterodyne signal, and the frequency associated with the highest peak may be considered equivalent to time lag $Rb/C_a$. Assuming that the frequency scan rate b and the speed of sound $C_a$ are known, the depth R may be estimated.

In some embodiments, a photoacoustic signal may be used with Eq. 1 to determine an absorption coefficient $\mu_a$. When a suitable light source is used (e.g., a photonic signal at 905 nm), tHb may be determined based on the value of the absorption coefficient and one or more pre-defined parameters. In some embodiments, a photonic signal may include light have two different wavelengths (e.g., one of which may be 905 nm), and blood oxygen saturation may be determined based on photoacoustic signals corresponding to the each wavelength of the photonic signal. In some embodiments, a light source may provide a photonic signal including light having a wavelength at an isobestic point where light absorption of oxy and de-oxy hemoglobin are substantially equal (e.g., at about 808 nm).

FIG. 1 is a perspective view of an embodiment of a physiological monitoring system 10. System 10 may include sensor unit 12, sensor unit 13, and monitor 14. In some embodiments, sensor units 12 and 13 may be part of a photoacoustic monitor or imaging system. Sensor units 12 and 13 may include respective light sources 16 and 15 for emitting light at one or more wavelengths, which may not need not correspond to visible light, into a subject's tissue. Light sources 16 and 15 may each provide a photonic signal that may include any suitable electromagnetic radiation such as, for example, a radio wave, a microwave wave, an infrared wave, a visible light wave, ultraviolet wave, any other suitable light wave, or any combination thereof. Detectors 18 and 17 may also be provided in sensor units 12 and 13, respectively, for detecting the acoustic (e.g., ultrasound) response that travels through the subject's tissue. Any suitable physical configuration of light sources 15 and 16, and detectors 17 and 18 may be used. In some embodiments, sensor unit 12 and/or sensor unit 13 may include multiple light sources and/or acoustic detectors, which may be spaced apart. It will be understood that although some of the details regarding photoacoustic sensors may be discussed with specific reference to sensor unit 12, any of the present disclosure may also apply to sensor unit 13, and any additional sensor units that may be included in system 10. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12 (e.g., a photoplethysmograph sensor). Multiple sensor units may be capable of being positioned at two different locations on a subject's body.

In some embodiments, system 10 may include two or more sensors forming a sensor array in lieu of either or both of the sensor units. In some embodiments, a sensor array may include multiple light sources, detectors, or both. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data relating to light emission and acoustic detection received from one or more sensor units such as sensor unit 12. For example, monitor 14 may be configured to determine cardiac output, intrathoracic blood volume, intrathoracic circulatory volume, global end-diastolic volume, pulmonary circulatory volume, extravascular lung water, any other suitable hemodynamic parameters, or any combination thereof. Further, monitor 14 may be configured to determine pulse rate, blood pressure, blood oxygen saturation (e.g., arterial, venous, or both), hemoglobin concentration (e.g., oxygenated, deoxygenated, and/or total), methemoglobin, carboxyhemoglobin, any other suitable physiological parameters, or any combination thereof. In some embodiments, calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a subject's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. Cable 24 may include electronic conductors (e.g., wires for transmitting electronic signals from detector 18), optical fibers (e.g., multi-mode or single-mode fibers for transmitting emitted light from light source 16), any other suitable components, any suitable insulation or sheathing, or any combination thereof. In some embodiments, cable 24 may be a single cable, which may couple to a single sensor having two or more elements (not shown in FIG. 1). In some embodiments, cable 24 may include two or more separate cables, which may couple to each of sensor units 12 and 13. In some embodiments, cable 24 may include a single cable that bifurcates from a single monitor connection to each of sensor units 12 and 13 (as shown in FIG. 1). In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may allow communication between monitor 14 and sensor unit 12.

In the illustrated embodiment, system 10 includes a multi-parameter physiological monitor 26. The monitor 26 may include a cathode ray tube display, a flat panel display (as shown) such as a liquid crystal display (LCD) or a plasma display, or may include any other type of monitor now known or later developed. Multi-parameter physiological monitor 26 may be configured to calculate physiological parameters and to provide a display 28 for information from monitor 14 and from other medical monitoring devices or systems (not shown). For example, multi-parameter physiological monitor 26 may be configured to display an estimate of a subject's extravascular lung water, cardiac output, and hemoglobin concentration generated by monitor 14. Multi-parameter physiological monitor 26 may include a speaker 30.

Monitor 14 may be communicatively coupled to multi-parameter physiological monitor 26 via a cable 32 or 34 that is coupled to a sensor input port or a digital communications port, respectively and/or may communicate wirelessly (not shown). In addition, monitor 14 and/or multi-parameter physiological monitor 26 may be coupled to a network to enable the sharing of information with servers or other workstations (not shown). Monitor 14 may be powered by a battery (not shown) or by a conventional power source such as a wall outlet.

Figure 2:
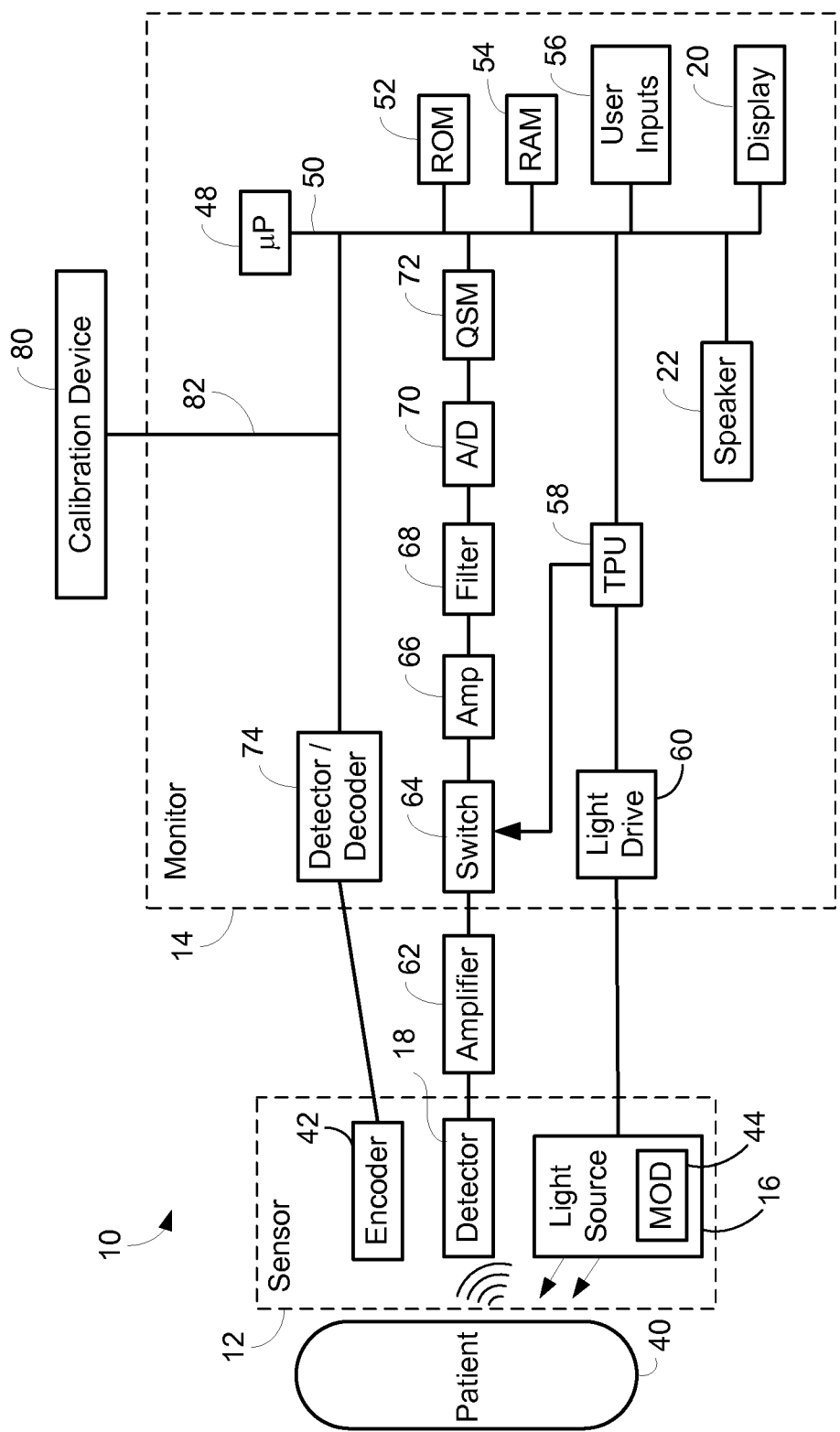
FIG. 2 is a block diagram of the illustrative physiological monitoring system of FIG. 1 coupled to a subject, in accordance with some embodiments of the present disclosure.

FIG. 2 is a block diagram of a physiological monitoring system, such as physiological monitoring system 10 of FIG. 1, which may be coupled to a subject 40 in accordance with an embodiment. Certain illustrative components of sensor unit 12 and monitor 14 are illustrated in FIG. 2. Although not shown in FIG. 2, system 10 may include additional sensor units such as, for example, sensor unit 13 of FIG. 1.

Sensor unit 12 may include light source 16, detector 18, and encoder 42. In some embodiments, light source 16 may be configured to emit one or more wavelengths of light (e.g., visible, infrared) into a subject's tissue 40. Hence, light source 16 may provide Red light, IR light, any other suitable light, or any combination thereof, that may be used to calculate the subject's physiological parameters. In some embodiments, a Red wavelength may be between about 600 nm and about 700 nm. In some embodiments, an IR wavelength may be between about 800 nm and about 1000 nm. In embodiments where a sensor array is used in place of a single sensor, each sensor may be configured to provide light of a single wavelength. For example, a first sensor may emit only a Red light while a second may emit only an IR light. In a further example, the wavelengths of light used may be selected based on the specific location of the sensor.

It will be understood that, as used herein, the term "light" may refer to energy produced by electromagnetic radiation sources. Light may be of any suitable wavelength and intensity, and modulations thereof, in any suitable shape and direction. Detector 18 may be chosen to be specifically sensitive to the acoustic response of the subject's tissue arising from use of light source 16. It will also be understood that, as used herein, the "acoustic response" shall refer to pressure and changes thereof caused by a thermal response (e.g., expansion and contraction) of tissue to light absorption by the tissue or constituent thereof.

In some embodiments, detector 18 may be configured to detect the acoustic response of tissue to the photonic excitation caused by the light source. In some embodiments, detector 18 may be a piezoelectric transducer which may detect force and pressure and output an electrical signal via the piezoelectric effect. In some embodiments, detector 18 may be a Faby-Pérot interferometer, or etalon. For example, a thin film (e.g., composed of a polymer) may be irradiated with reference light, which may be internally reflected by the film. Pressure fluctuations may modulate the film thickness, thus causing changes in the reference light reflection which may be measured and correlated with the acoustic pressure. In some embodiments, detector 18 may be configured or otherwise tuned to detect acoustic response in a particular frequency range. Detector 18 may convert the acoustic pressure signal into an electrical signal (e.g., using a piezoelectric material, photodetector of a Faby-Pérot interferometer, or other suitable device). After converting the received acoustic pressure signal to an electrical, optical, and/or wireless photoacoustic signal, detector 18 may send the photoacoustic signal to monitor 14, where physiological parameters may be calculated based on the photoacoustic activity within the subject's tissue 40.

In some embodiments, encoder 42 may contain information about sensor unit 12, such as what type of sensor it is (e.g., where the sensor is intended to be placed on a subject), the wavelength(s) of light emitted by light source 16, the intensity of light emitted by light source 16 (e.g., output wattage or Joules), the mode of light source 16 (e.g., pulsed versus CW), any other suitable information, or any combination thereof. This information may be used by monitor 14 to select appropriate algorithms, lookup tables and/or calibration coefficients stored in monitor 14 for calculating the subject's physiological parameters.

Encoder 42 may contain information specific to subject 40, such as, for example, the subject's age, weight, and diagnosis. This information about a subject's characteristics may allow monitor 14 to determine, for example, subject-specific threshold ranges in which the subject's physiological parameter measurements should fall and to enable or disable additional physiological parameter algorithms. Encoder 42 may, for instance, be a coded resistor that stores values corresponding to the type of sensor unit 12 or the type of each sensor in the sensor array, the wavelengths of light emitted by light source 16 on each sensor of the sensor array, and/or the subject's characteristics. In some embodiments, encoder 42 may include a memory on which one or more of the following information may be stored for communication to monitor 14: the type of the sensor unit 12; the wavelengths of light emitted by light source 16; the particular acoustic range that each sensor in the sensor array is monitoring; the particular acoustic spectral characteristics of the detector; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, any other type of non-volatile storage such as flash, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control the activation of light source 16. For example, TPU 58 may control pulse timing (e.g., pulse duration and inter-pulse interval) for TD-PA monitoring system. TPU 58 may also control the gating-in of signals from detector 18 through amplifier 62 and switching circuit 64. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIGS. 1-2) coupled by bus 50 or otherwise coupled (e.g., via an external bus), may be referred to as "processing equipment."

In the embodiment shown, light source 16 may include modulator 44, in order to, for example, perform FD-PA analysis. Modulator 44 may be configured to provide intensity modulation, spatial modulation, any other suitable optical signal modulations, or any combination thereof. For example, light source 16 may be a CW light source, and modulator 44 may provide intensity modulation of the CW light source such as using a linear sweep modulation. In some embodiments, modulator 44 may be included in light drive 60, or other suitable components of physiological monitoring system 10, or any combination thereof.

In some embodiments, microprocessor 48 may determine the subject's physiological parameters, such as $SpO_2$, $SvO_2$, oxy-hemoglobin concentration, deoxy-hemoglobin concentration, total hemoglobin concentration (tHb), pulse rate, cardiac output, intrathoracic blood volume, intrathoracic circulatory volume, global end-diastolic volume, pulmonary circulatory volume, extravascular lung water, and/or other physiological parameters, using various algorithms and/or lookup tables based on the value of the received signals and/or data corresponding to the acoustic response received by detector 18. Signals corresponding to information about subject 40, and particularly about the acoustic signals emanating from a subject's tissue over time, may be transmitted from encoder 42 to decoder 74. These signals may include, for example, encoded information relating to subject characteristics. Decoder 74 may translate these signals to enable the microprocessor to determine the thresholds based at least in part on algorithms or lookup tables stored in ROM 52. In some embodiments, user inputs 56 may be used to enter information, select one or more options, provide a response, provide input settings, provide any other suitable inputting function, or any combination thereof. User inputs 56 may be used to enter information about the subject such as, for example, age, weight, height, diagnosis, medications, treatments, and so forth. In some embodiments, display 20 may exhibit a list of values, which may generally apply to the subject, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

The acoustic pressure signal attenuated by the tissue of subject 40 can be degraded by noise, among other sources. Movement of the subject may also introduce noise and affect the signal. For example, the contact between the detector and the skin, or the light source and the skin, can be temporarily disrupted when movement causes either to move away from the skin. Another potential source of noise is electromagnetic coupling from other electronic instruments.

Noise (e.g., from subject movement) can degrade a sensor signal relied upon by a care provider, without the care provider's awareness. This is especially true if the monitoring of the subject is remote, the motion is too small to be observed, or the care provider is watching the instrument or other parts of the subject, and not the sensor site. Processing sensor signals may involve operations that reduce the amount of noise present in the photoacoustic signals, control the amount of noise present in the photoacoustic signal, or otherwise identify noise components in order to prevent them from affecting measurements of physiological parameters derived from the photoacoustic signals.

Figure 3:
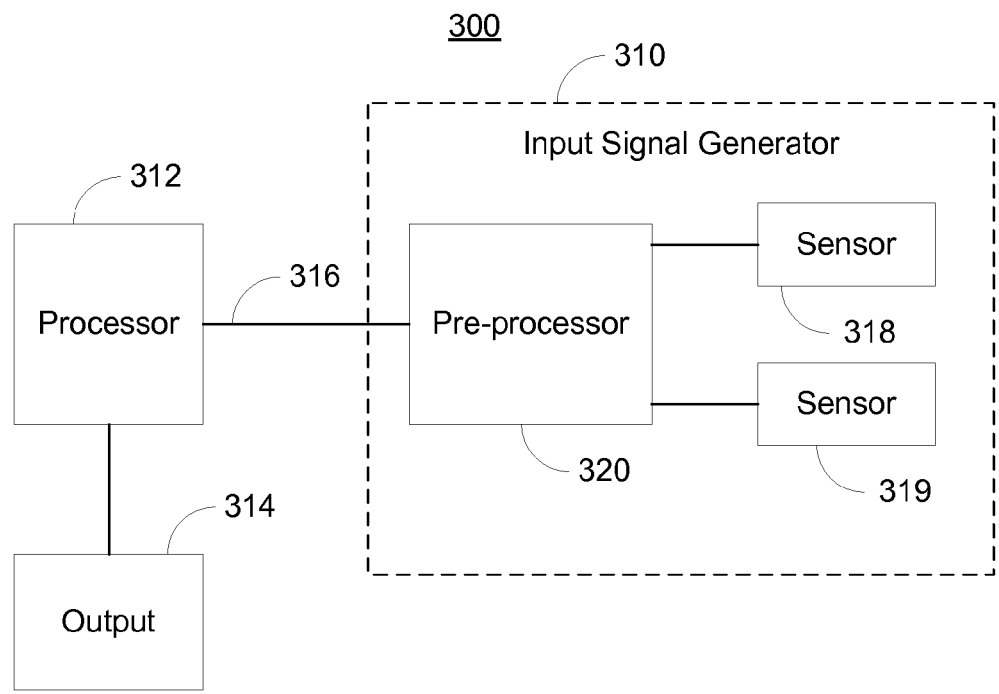
FIG. 3 is a block diagram of an illustrative signal processing system, in accordance with some embodiments of the present disclosure.

FIG. 3 is an illustrative signal processing system 300 in accordance with an embodiment that may implement the signal processing techniques described herein. In some embodiments, signal processing system 300 may be included in a physiological monitoring system (e.g., physiological monitoring system 10 of FIGS. 1-2). In the illustrated embodiment, input signal generator 310 generates an input signal 316. As illustrated, input signal generator 310 may include pre-processor 320 coupled to sensor 318 and sensor 319, and any suitable additional sensors (not shown), which may provide input signal 316. In some embodiments, pre-processor 320 may be a photoacoustic module and input signal 316 may be a photoacoustic signal. In an embodiment, pre-processor 320 may be any suitable signal processing device and input signal 316 may include one or more photoacoustic signals and one or more other physiological signals, such as a photoplethysmograph signal. It will be understood that input signal generator 310 may include any suitable signal source, signal generating data, signal generating equipment, or any combination thereof to produce input signal 316. Input signal 316 may be a single signal, or may be multiple signals transmitted over a single pathway or multiple pathways.

Sensors 318 and 319 may each include one or more light sources, which may each provide a photonic signal that may include any suitable electromagnetic radiation such as, for example, a radio wave, a microwave wave, an infrared wave, a visible light wave, ultraviolet wave, any other suitable light wave, or any combination thereof. Sensors 318 and 319 may each include one or more acoustic detectors for detecting the acoustic pressure (e.g., ultrasound) response that travels through the subject's tissue. Any suitable physical configuration of light sources and detectors may be used. In some embodiments, sensor 318 and/or sensor 319 may include multiple light sources and/or acoustic detectors, which may be spaced apart. In some embodiments (not shown), a single sensor may be used, which may include one or more light sources and multiple detectors. For example, in some embodiments, one or more light sources may be used to provide one or more photonic signals, and a detector array including multiple detectors may be used to detect acoustic pressure signals. System 300 may include any suitable number of sensors.

Pre-processor 320 may apply one or more signal processing operations to the signals generated by sensor 318 and sensor 319. For example, pre-processor 320 may apply a pre-determined set of processing operations to the signal provided by sensor 318 and/or sensor 319 to produce input signal 316 that can be appropriately interpreted by processor 312, such as performing A/D conversion. In some embodiments, A/D conversion may be performed by processor 312. Pre-processor 320 may also perform any of the following operations on the signal provided by sensor 318 and/or sensor 319: reshaping the signal for transmission, multiplexing the signal, modulating the signal onto carrier signals, compressing the signal, encoding the signal, and filtering the signal. In some embodiments (not shown), sensor 318 and sensor 319 may be coupled to separate pre-processors, which may each provide an input signal to processor 312. Any suitable number of sensors may be included as part of system 300, coupled to any suitable number of pre-processors. In some embodiments, two or more independent photoacoustic systems may be used, in accordance with the present disclosure. In some embodiments, the more than one photoacoustic systems may each include one or more sensor units. In some such embodiments, each photoacoustic system may output a photoacoustic signal and/or waveform. The outputted photoacoustic signal and/or waveform may be further processed by either of the photoacoustic systems, a monitor, any other suitable device, or any combination thereof. Any suitable arrangement of one or more sensor units, and processing equipment, may be used in accordance with the present disclosure.

In some embodiments, input signal 316 may be coupled to processor 312. Processor 312 may be any suitable software, firmware, hardware, or combination thereof for processing signal 316. For example, processor 312 may include one or more hardware processors (e.g., integrated circuits), one or more software modules, and computer-readable media such as memory, firmware, or any combination thereof. Processor 312 may, for example, be a computer or may be one or more chips (i.e., integrated circuits) such as, for example, a field programmable gate array (FPGA), micro-controller, or digital signal processor (DSP). Processor 312 may, for example, include an assembly of analog electronic components. Processor 312 may calculate physiological information. For example, processor 312 may perform time domain calculations, spectral domain calculations, time-spectral transformations (e.g., fast Fourier transforms, inverse fast Fourier transforms), any other suitable calculations, or any combination thereof. Processor 312 may perform any suitable signal processing of input signal 316 to filter input signal 316, such as any suitable band-pass filtering, adaptive filtering, closed-loop filtering, any other suitable filtering, and/or any combination thereof. Processor 312 may also receive input signals from additional sources (not shown). For example, processor 312 may receive an input signal containing information about treatments provided to the subject. Additional input signals may be used by processor 312 in any of the calculations or operations it performs in accordance with processing system 300.

In some embodiments, all or some of pre-processor 320, processor 312, or both, may be referred to collectively as processing equipment. In some embodiments, any of the processing components and/or circuits, or portions thereof, of FIGS. 1-3 may be referred to collectively as processing equipment. For example, processing equipment may be configured to amplify, filter, sample and digitize input signal 316 (e.g., using an analog to digital converter), and calculate physiological information from the digitized signal. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal.

Processor 312 may be coupled to one or more memory devices (not shown) and/or incorporate one or more internal memory devices such as any suitable volatile memory device (e.g., RAM, registers, etc.), non-volatile memory device (e.g., ROM, EPROM, magnetic storage device, optical storage device, flash memory, etc.), or both. In some embodiments, processor 312 may store physiological measurements or previously received data from input signal 316 in a memory device for later retrieval. In some embodiments, processor 312 may store calculated values, such as pulse rate, blood pressure, blood oxygen saturation (e.g., arterial, venous, or both), hemoglobin concentration (e.g., oxygenated, deoxygenated, and/or total), cardiac output, intrathoracic blood volume, intrathoracic circulatory volume, global end-diastolic volume, pulmonary circulatory volume, extravascular lung water, or any other suitable calculated values, or combinations thereof, in a memory device for later retrieval.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof. In some embodiments, processor 312 may drive a display such as, for example, an LCD display, and accept input directly from a user interface including pushbuttons and/or a touchscreen displaying one or more soft command buttons.

In some embodiments, sensor 318 and/or sensor 319 may include a pulsed light source, which may provide a series of photonic pulses to a monitoring site. In some such embodiments, points of acoustic pressure signals corresponding to more than one light pulse may be combined (e.g., ensemble averaged or summed) to increase a signal to noise ratio. For example, for each photonic pulse, a particular point of an acoustic pressure signal may correspond to a peak pressure from a particular spatial location (e.g., a blood vessel site, characterized by a particular time lag due to the travel time of acoustic waves in tissue). A photoacoustic signal may include, for example, a collection of these particular points, or a collection of moving averages of these particular points. In some embodiments, sensor 318 and/or sensor 319 may include a frequency modulated CW light source, which may provide a periodic photonic signal, having constant (e.g., sinusoidal) or changing (e.g., a chirp) periodicity, to a monitoring site. In some such embodiments, points of acoustic pressure signals corresponding to a particular modulation frequency may be averaged in time to increase a signal to noise ratio. For example, for each particular modulation frequency, a particular point of an acoustic pressure signal may correspond to a peak pressure from a particular spatial location (e.g., a blood vessel site, characterized by a particular time lag due to the travel time of acoustic waves in tissue), occurring at the peaks of the photonic signal. A photoacoustic signal may include, for example, a collection of these particular points, or a collection of moving averages of these particular points.

In some embodiments, processing equipment of system 300 may analyze input signal 316 and/or other signals that may arise from a photoacoustic response. In some embodiments, processing equipment of system 300 may determine one or more signal confidence values. Signal confidence values may include, or be based in part on, a signal to noise ratio of a photoacoustic signal and/or an acoustic pressure signal, a difference between two photoacoustic signals or dilution curves derived thereof, a signal amplitude, a signal standard deviation, a signal noise baseline, any other suitable signal confidence metric, or any combination thereof.

It will be understood that system 300 may be incorporated into system 10 (FIGS. 1 and 2) in which, for example, input signal generator 310 may be implemented as part of sensor unit 12 (FIGS. 1 and 2) and monitor 14 (FIGS. 1 and 2) and processor 312 may be implemented as part of monitor 14 (FIGS. 1 and 2). In some embodiments, portions of system 300 may be configured to be portable. For example, all or part of system 300 may be embedded in a small, compact object carried with or attached to the subject (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous physiological monitoring solution. In some embodiments, a wireless transceiver (not shown) may also be included in system 300 to enable wireless communication with other components of system 10. For example, pre-processor 320 may output input signal 316 (e.g., which may be a pre-processed photoacoustic signal) over BLUETOOTH, IEEE 802.11, WiFi, WiMax, cable, satellite, Infrared, any other suitable transmission scheme, or any combination thereof. In some embodiments, a wireless transmission scheme may be used between any communicating components of system 300.

It will also be understood that while some of the equations referenced herein are continuous functions, the processing equipment may be configured to use digital or discrete forms of the equation in processing the acquired PA signal.

Figure 4:
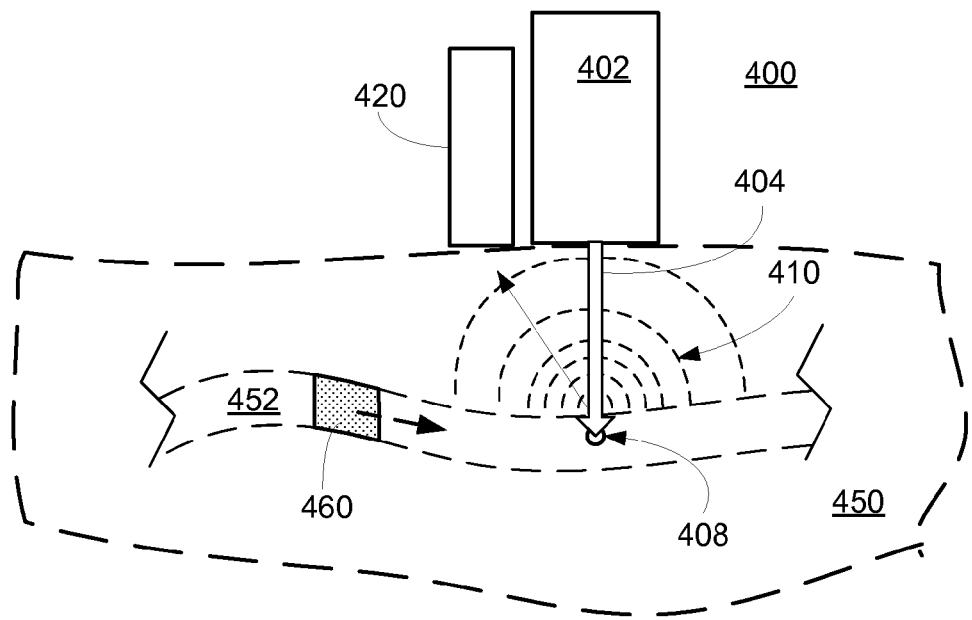
FIG. 4 shows an illustrative photoacoustic arrangement, in accordance with some embodiments of the present disclosure.

FIG. 4 shows an illustrative photoacoustic arrangement 400, in accordance with some embodiments of the present disclosure. Light source 402, controlled by a suitable light drive (e.g., a light drive of system 300 or system 10, although not shown in FIG. 4), may provide photonic signal 404 to subject 450. Photonic signal 404 may be attenuated along its pathlength in subject 450 prior to reaching site 408 of blood vessel 452, and may be attenuated across blood vessel 452. It will be understood that photonic signal 404 may scatter in subject 450 and need not travel as a constant, well-formed beam as illustrated. Also, photonic signal 404 may generally travel through and beyond site 408, although not illustrated in FIG. 4. A constituent of the blood in blood vessel 452 such as, for example, hemoglobin, or an injected indicator (e.g., a dye) may absorb at least some of photonic signal 404 at site 408. Accordingly, the blood may exhibit an acoustic pressure response via the photoacoustic effect, which may act on the surrounding tissues of blood vessel 452. Acoustic detector 420 may detect acoustic pressure signals 410 traveling though tissue of subject 450, and along with suitable processing equipment output (not shown) a photoacoustic signal that may be processed by suitable processing equipment. Changes in some properties of the blood in blood vessel 452 at site 408 may be detected by acoustic detector 420. For example, a reduced hemoglobin concentration or reduced temperature at the monitoring site may cause a reduced acoustic pressure signal to be detected by acoustic detector 420. In some embodiments, bolus dose 460, which may include a suitable indicator, may be introduced to the blood of patient 450 at a suitable blood vessel site (not shown in FIG. 4). Acoustic detector 420 may detect the transient changes in the hemoglobin concentration ("hemo-dilution") and/or temperature ("thermo-dilution") at site 408 due to passage of bolus dose 460 through site 408. In some embodiments, multiple monitoring sites (not shown) may be used to detect changes in hemoglobin concentration, temperature, or both. As bolus dose 460 travels through the circulatory system of subject 450, diffusion, mixing (e.g., within a heart chamber), or both may spread the hemoglobin concentration and temperature profiles axially (i.e., in the direction of flow) and radially (i.e., normal to the direction of flow). It will be understood that hemo-dilution refers to the dilution of blood constituents caused by the bolus dose, and thermo-dilution refers to the combined effects of blood constituent dilution and temperature change, both caused by the bolus dose. In some embodiments, using a thermo-dilution indicator, a temperature change may be enhanced by hemo-dilution (e.g., when the temperature change and the dilution change both cause the photoacoustic signal to either increase or decrease), and accordingly may be detected by a system having relatively less temperature sensitivity.

Dilution techniques using a bolus dose may be used to determine, for example, cardiac output (CO), intrathoracic blood volume (ITBV), intrathoracic circulatory volume (ITCV), global end-diastolic volume (GEDV), pulmonary circulatory volume (PCV), extravascular lung water (EVLW), and/or other hemodynamic parameters.

A bolus dose of an indicator may cause the properties at a photoacoustic monitoring site to change in time as the bolus dose passes the site. Introduction of the indicator may alter one or more properties of the blood that interacts with the indicator (e.g., blood near the bolus dose). An indicator introduced as a bolus dose may be selected to have one or more properties that allow the bolus dose to be distinguished from a subject's un-dosed blood. For example, an indicator may be selected which has particular absorption properties at one or more particular wavelengths (e.g., a dye indicator such as indocyanine green dye), and the photoacoustic monitoring system may monitor the presence of the indicator by providing a photonic signal at one or more particular wavelengths and detecting an acoustic pressure signal having a dye indicator dilution response. In a further example, an indicator may be selected to dilute blood of a subject but not substantially absorb the photonic signal. The photoacoustic monitoring system may then accordingly monitor the blood (e.g., hemoglobin) rather than the indicator, to detect dilution. In a further example, an indicator having a temperature different from the temperature of the subject's un-dosed blood may be introduced into a subject's bloodstream (e.g., a "hot" or "cold" indicator, relative to the blood temperature). The photoacoustic monitoring system may then accordingly monitor the bloodstream temperature at the monitoring site, or the combined effects of hemo-dilution and thermo-dilution achieved by the bolus dose. In some embodiments, an indicator may have more than one property that may be distinguished from a subject's blood. For example, a cold dye indicator may be introduced to the subject's bloodstream, which may allow hemo-dilution and thermo-dilution effects to be detected. In some embodiments, more than one indicator may be introduced to the subject's bloodstream, each indicator having particular properties that may be unique relative to the other indicators. For example, an isotonic indicator and a hypertonic indicator may be introduced into a subject's bloodstream. In a further example, a cold isotonic indicator and a dye indicator may be introduced into a subject's bloodstream. An indicator may include saline (e.g., isotonic, hypertonic, hypotonic), dye (e.g., indocyanine), lithium, any other suitable chemical or mixture, or any combination thereof.

In some embodiments, a relatively small amount of indicator may be introduced to a subject's bloodstream. For example, a bolus dose on the order of 10 mL may be injected to act as an indicator. Accordingly, the detected response may be relatively small. For example, the temperature change caused by a thermo-dilution indicator may be less than 1° Celsius, depending on the amount of indicator used and the monitoring arrangement used.

Figure 5:
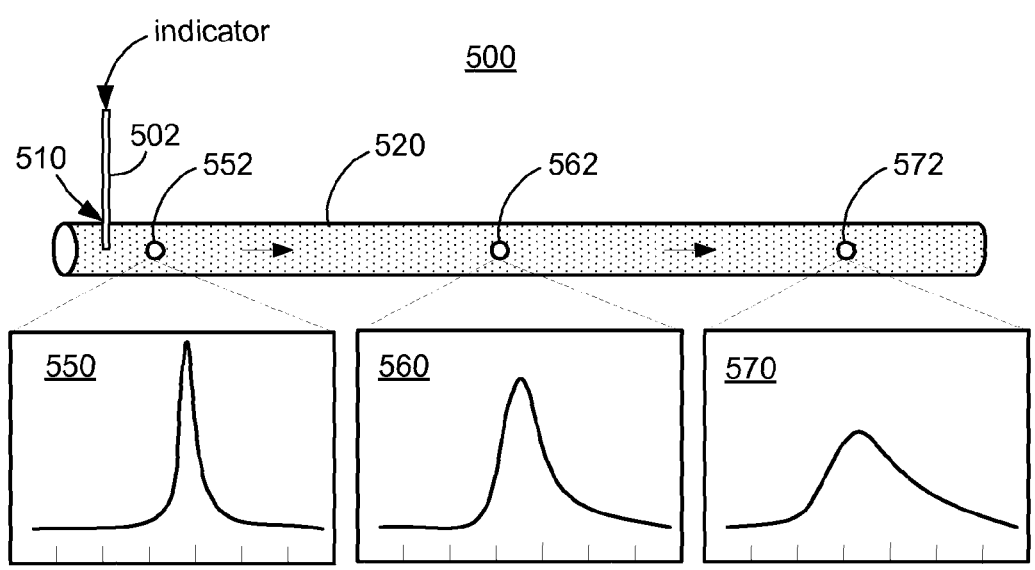
FIG. 5 shows an illustrative indicator arrangement, in accordance with some embodiments of the present disclosure.

FIG. 5 shows an illustrative indicator arrangement 500, in accordance with some embodiments of the present disclosure. In some embodiments, an indicator may be provided to the circulatory system of a subject to aid in determining one or more physiological parameters. For example, a saline solution may be injected into a subject's circulatory system at blood vessel site 510 using needle 502. Blood vessel site 510 may be located at any suitable portion of a subject's circulatory system such as a vein, an artery, a capillary, or other suitable location. For example, blood vessel site 510 may be a central vein of the subject. Portion 520 of the subject's circulatory system shown illustratively in FIG. 5 may include heart chambers, arteries, veins, capillaries, any other suitable parts of the circulatory system, or any combination thereof. As the indicator travels along portion 520, in the direction of the motion arrows away from the introduction site, the concentration and/or temperature profile of may change. For example, panel 550 shows an illustrative dilution curve time series as detected at site 552, relatively near site 510. Panels 560 and 570 each show illustrative time series of dilution curves at sites 562 and 572, respectively, both downstream from site 552. The dilution curve shown in panel 560 is relatively flattened in time compared to the dilution curve shown in panel 550. The dilution curve shown in panel 570 is relatively flattened in time compared to the dilution curve shown in panel 560. The flattening may be due to diffusion and mixing of the indicator with the subject's blood. The area under the time series of panels 550, 560, and 570 may be, but need not be, the same and may depend on the indicator type, travel time, site location, and other suitable variables. The phrase "dilution curve" as used herein shall refer to a time series, continuous or discrete, indicative of dilutive effects of an indicator on the concentration of blood constituents and/or blood temperature. For example, a dilution curve may include a time series of concentration or changes thereof of a blood constituent, an indicator, or both. In a further example, a dilution curve may include a time series of temperature, or change in temperature, of blood of the subject at a monitoring site. As the indicator is transported through the subject's vasculature, a portion of the indicator may travel through each blood vessel, proportional to the flow rate of blood in that vessel. Accordingly, the original bolus dose of indicator may "mix out" after some time, and a steady-state, or near steady-state condition may be achieved (e.g., similar to a steady-state or near steady-state condition before the bolus dose was introduced).

Figure 6:
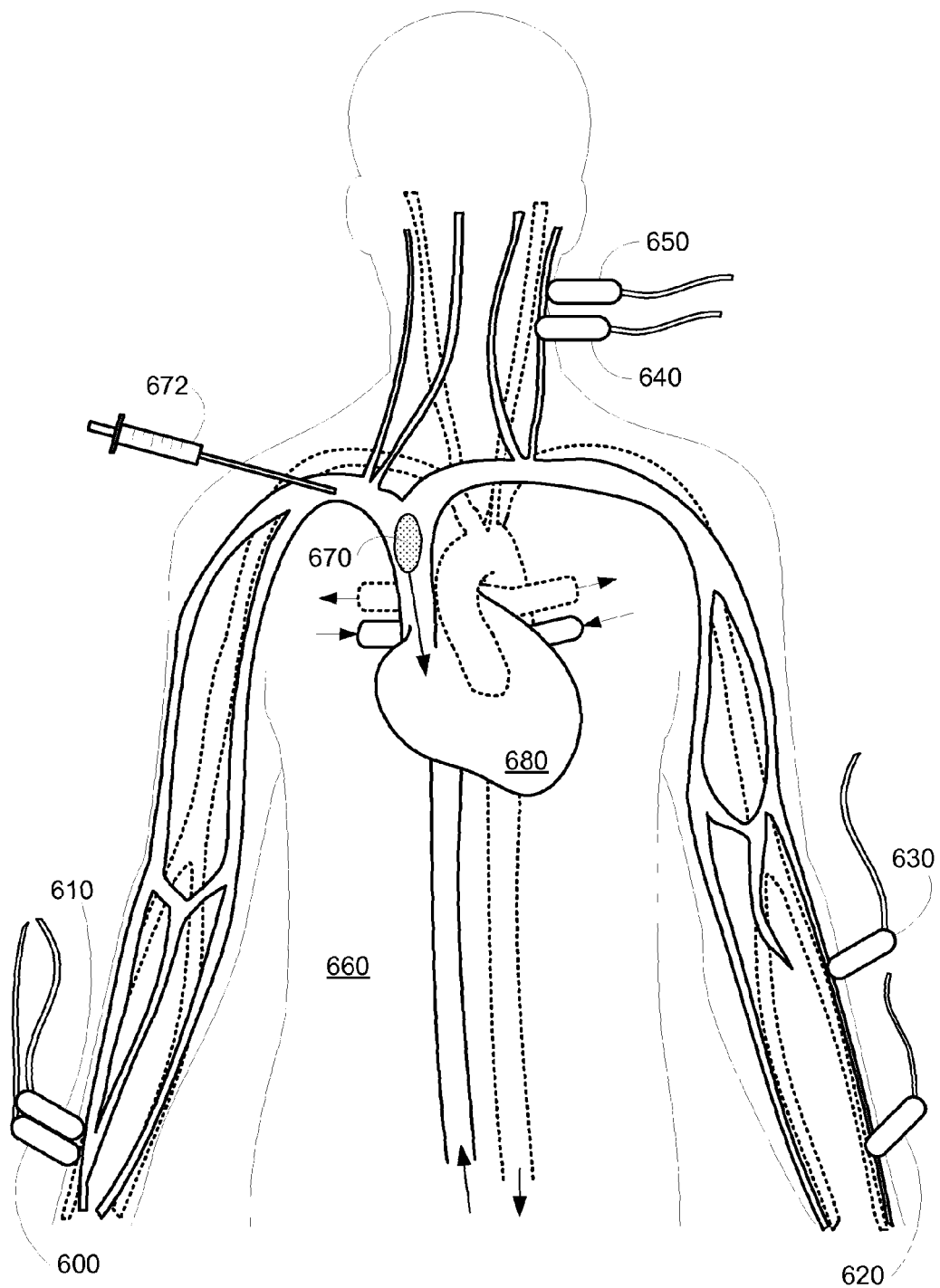
FIG. 6 shows several illustrative arrangements of sensor units on a subject relative to the subject's vasculature, as well as a bolus dose, in accordance with some embodiments of the present disclosure.

FIG. 6 shows several illustrative arrangements of sensor units 600, 610, 620, 630, 640, and 650 on a subject 660 relative to the subject's vasculature, as well as a simplified illustration of a bolus dose 670, in accordance with some embodiments of the present disclosure. A portion of the vasculature of subject 660 is shown illustratively in FIG. 6, in which vessels having solid lines correspond to venous vessels and vessels having dashed lines correspond to arterial vessels. Bolus dose 670, which includes an indicator, may be introduced to subject 660 at a suitable site (shown as the superior vena cava in FIG. 6) using injector 672. Injector 672 may include a hypodermic needle, a peripheral cannula, a central intra-venous (IV) line, any other suitable IV or arterial catheter, or any combination thereof. In the illustrated embodiment, bolus dose 670 may circulate through the vasculature, heart 680, and lungs (not shown) of subject 660, and spread over time (e.g., due to mixing, diffusion, and bifurcating vessels), and may be detected at one or more sites using a photoacoustic monitoring system, such as, for example, system 10 of FIGS. 1-2 and/or system 300 of FIG. 3. Sensor units 600, 610, 620, 630, 640, and 650 may be placed on the subject's skin, near a blood vessel of interest.

One or more arrangements of sensor units may be used to detect an indicator response, as shown in FIG. 6. Acoustic pressure signals, and/or photoacoustic signals derived thereof, may include the effects of multiple blood vessels, indicator responses, or both. In some embodiments, a single photoacoustic sensor may provide relatively low signal amplitude, resolution and/or signal to noise ratio. The illustrative arrangements of FIG. 6 may aid in increasing signal to noise ratio, spatial resolution, temporal resolution, signal confidence, and/or signal amplitude. Some arrangements of FIG. 6 may aid in distinguishing acoustic pressure signals, or components thereof, arising from different blood vessels. For example, in some circumstances, it may be challenging to differentiate photoacoustic signals from close-by vessels, such as a carotid artery and internal jugular vein using a single wavelength (e.g., 905 nm) measurement when a single sensor is placed on the neck.

For example, sensor units 600 and 610 are located at substantially the same site, near the radial artery (shown by the vessel having dotted lines) of subject 660. It will be understood that the phrase "substantially the same site" shall refer to an arrangement of sensor units with respective monitoring sites that exhibit substantially the same indicator response, at the same blood vessel, as compared to the effects of mixing, diffusion and bifurcating vessels. In some circumstances, the spacing of monitoring sites that may be considered the "same site" may depend on a blood vessel diameter, depth of the blood vessel, any other suitable parameters, or any combination thereof. In general, closer spacing of the sites may be preferred to improve signal to noise ratio (SNR). In some embodiments, the photoacoustic signals outputted by sensor units 600 and 610 may be averaged (e.g., ensemble averaged), summed, differenced, compared, or otherwise used in concert by system 10 and/or system 300. In some embodiments, one or more physiological parameters determined separately based on the respective photoacoustic signals outputted by sensor units 600 and 610 may be averaged (e.g., ensemble averaged), summed, differenced, compared, or otherwise used in concert by system 10 and/or system 300. The use of two measurements at substantially the same site may aid in increasing the SNR of the detected acoustic pressure signals. In some embodiments, SNR may be determined by weighting relative amplitudes of dilution curves derived from each of sensor units 600 and 610. In some embodiments, determining SNR may include determining a noise baseline of each of sensor units 600 and 610. In some embodiments, sensor units 600 and 610 may be placed as close as possible to one another, so that their respective monitoring sites are coincident or nearly coincident. In some embodiments, the photoacoustic signal exhibiting the lowest relative indicator response magnitude may be discarded. For example, if a photoacoustic signal from sensor unit 600 exhibits a larger magnitude than a photoacoustic signal from sensor unit 610, processor 312 may use signals from sensor unit 600 solely to determine physiological information. In some embodiments, if a photoacoustic signal from sensor unit 600 exhibits a larger magnitude than a photoacoustic signal from sensor unit 610, processor 312 may weight the signal of sensor unit 600 more than sensor unit 610 when determining an average (e.g., a weighted average). The weights may be, but need not be, based on a signal confidence (e.g., a signal to noise ratio of the signal). For example, if sensor unit 610 measures a maximum change of 0.2° C. and sensor unit 600 measures 0.5° C., then more weight may be put on signals from sensor unit 600. In some embodiments, processor 312 may determine a difference between the photoacoustic signals of sensor units 600 and 610. For example, a third sensor (not shown) may be included at substantially the same site as sensor units 600 and 610. The photoacoustic signal of the sensor unit differing most (e.g., in shape, value, or other property) from the other two signals (e.g., based on a difference, or statistical calculation) may be discarded, and the remaining two signals may be further processed. In some embodiments, the differences in photoacoustic signals may be indicative of differences in placement (e.g., distance between monitoring sites of sensor units). For example, if sensor units 600 and 610 are placed 1 cm apart, differences in the respective photoacoustic signals may be indicative of a travel distance of 1 cm. In some embodiments, processor 312 may perform a cross-correlation to determine a time delay between features of the photoacoustic signals of sensor units 600 and 610. After applying a suitable time shift to account for the time delay, the signals may then be averaged, summed, and/or compared. In some embodiments, sensor units 600 and 610 may be configured to detect acoustic pressure signals arising from photonic signals in or out of phase relative to one another. In some such embodiments, sensor units 600 and 610 may each detect at the same sampling rate, out of phase by a half period, so that the effective sample rate is doubled (e.g., achieving a sample rate of 50-100 Hz). Using out of phase detection and/or processing may aid in preventing under-sampling of an indicator response. In some embodiments, sensor units 600 and 610 may each detect at the same sampling rate, in phase, and the corresponding photoacoustic signals may be averaged, summed or otherwise combined. In some such embodiments, the corresponding light sources may be activated in phase, increasing the photonic excitation at a monitoring site. Because the light sources are spatially spaced, some such arrangements may aid in providing the photonic signal to the subject without overheating the subject's tissue due to higher photonic intensity. In some embodiments, processing equipment may generate the photoacoustic signals at the same sampling rate, in phase, and the corresponding photoacoustic signals may be averaged, summed or otherwise combined.

In a further example, sensor units 600 and 620 are located at similar sites near the respective right and left radial arteries (shown by the vessels having dotted lines) of subject 660. The photoacoustic signals from sensor units 600 and 620 may be averaged (e.g., ensemble averaged), summed, compared, or otherwise used in concert by system 10 and/or system 300. The use of two measurements at similar sites (e.g., on the right and left sides of subject 660) may aid in increasing the signal confidence (e.g., SNR), detecting a fault, performing a diagnostic test (e.g., testing that sensor units 600 and 620 are both operational), indicating a pathlength of the subject's vasculature, setting a signal baseline, or other processing of the photoacoustic signals. In some embodiments, the photoacoustic signal exhibiting the lowest relative indicator response magnitude may be discarded. For example, if a photoacoustic signal from sensor unit 600 exhibits a larger magnitude than a photoacoustic signal from sensor unit 620, processor 312 may use signals from sensor unit 600 solely to determine physiological information. In a further example, if a photoacoustic signal from sensor unit 600 exhibits a larger magnitude than a photoacoustic signal from sensor unit 620, processor 312 may weight the photoacoustic signal from sensor unit 600 more than the photoacoustic signal from sensor unit 620 when determining an average (e.g., a weighted average). In some embodiments, processor 312 may perform a cross-correlation to determine a time delay between the detected indicator responses of photoacoustic signals of sensor units 600 and 620. After applying a suitable time shift to account for the time delay, the photoacoustic signals may then be averaged and/or compared. In some embodiments, the time delay may be used by processor 312 to determine path information regarding the vasculature of subject 660. In some embodiments, differences between the photoacoustic signals from sensor units 600 and 620, or indicator dilution curves derived thereof, may indicate differences in warming along the respective vasculature paths, differences in relative perfusion of the two sites, any other suitable differences, or any combination thereof. In some embodiments, differences between the photoacoustic signals from sensor units 600 and 620 may be used as a baseline indicator, and deviations in the time delay between signals from the sensor units may indicate physiological changes. This indication may be useful, for example, during the course of a surgery.

In a further example, sensor units 630 and 620 are located at different sites along the same radial artery (shown by the vessel having dotted lines) of subject 660. The acoustic pressure signals detected by sensor units 630 and 620 may include indicator responses, which may exhibit different characteristics. For example, as bolus dose 670 passes through the monitoring site of sensor unit 630, a photoacoustic signal derived from the detected acoustic pressure signal may exhibit an indicator response (e.g., a peak and/or trough). As bolus dose 670 passes through the monitoring site of sensor unit 620, which is located distal to sensor unit 630 relative to the heart 680, the photoacoustic signal derived from detected acoustic pressure signal may also exhibit an indicator response (e.g., a peak and/or trough) although the shape may be different. As bolus dose 670 travels through the radial artery, the temporal concentration profile and/or temperature profile may flatten, decreasing in magnitude and increasing in width. In some embodiments, bolus dose 670 may include a thermo-dilution indicator. Sensor unit 630 may detect a first response to the thermo-dilution indicator. As the thermo-dilution indicator travels from the monitoring site of sensor unit 630 to the monitoring site of sensor unit 620, the temperature may gradient may be relatively reduced, although the concentration gradient (e.g., the concentration of the indicator such as saline) may remain relatively constant. Accordingly, the effects of thermo-dilution and hemo-dilution may be distinguished and/or separated using the arrangement of sensor units 630 and 620. In some embodiments, processing equipment of system 300 may use differences between the photoacoustic signals from sensor units 630 and 620 to provide an estimate of the effects of hemo-dilution alone as compared to the combined effects of hemo-dilution and thermo-dilution. In some embodiments, the time delay between the indicator responses detected by sensor units 630 and 620 may be used to determine a blood flow rate and, for example, estimate cardiac output. In addition to or in place of the illustrated elbow and wrist arrangement, sensor units 630 and 620 may also (not shown) be arranged, for example, at the shoulder and corresponding wrist of the subject, head to wrist, neck to wrist, or any other locations distal to one another relative to the left ventricle of the heart. In some embodiments, for example, a temple site may be used rather than a wrist site.

As shown in FIG. 6, sensor units 600, 610, 620, and 630 are configured to monitor the radial artery, although any suitable blood vessel may be monitored in accordance with the techniques disclosed herein.

In a further example, sensor units 640 and 650 may be placed at the neck of subject 660, near a carotid artery and a jugular vein, respectively. The monitoring site may include both the carotid artery and nearby jugular vein. For example, as bolus dose 670 passes through the blood vessel site of sensor unit 640, a photoacoustic signal derived from the detected acoustic pressure signal may exhibit an indicator response (e.g., a peak and/or trough). As bolus dose 670 passes through the brain tissue, and then to the blood vessel site of sensor unit 650, which is located at a jugular vein of subject 660, a photoacoustic signal derived from the detected acoustic pressure signal may also exhibit an indicator response (e.g., a peak and/or trough) although the shape may be different. As bolus dose 670 travels through the brain tissue, the temporal concentration profile and/or temperature profile may flatten, decreasing in magnitude and increasing in width. Accordingly, the time delay and/or change in shape may be used to distinguish the indicator response of the arterial site from the indicator response of the venous site.

In a further example, sensor unit 640, which may include one or more light sources and one or more acoustic detectors (e.g., a sensor array), may be placed at the neck of subject 660, near both a carotid artery and a jugular vein. Sensor unit 640 may detect acoustic pressure signals from both the carotid artery and the jugular vein. As bolus does 670 passes through the carotid monitoring site, a photoacoustic signal derived from the acoustic pressure signal detected by sensor unit 640 may exhibit an indicator response. After traveling through the brain tissue of subject 660, bolus dose 670 may pass through the jugular monitoring site. Sensor unit 640 may detect an acoustic pressure signal, and a photoacoustic signal derived thereof may exhibit another indicator response, although shifted in time relative to the response at the arterial site. In some embodiments, processor 312 may use the time shift, which may be calculated using a cross-correlation of the two indicator responses, to distinguish the arterial response form the relatively later venous response (e.g., when using more than one detector). In some embodiments, sensor unit 640 may detect an acoustic pressure signal, which may include pressure responses of arterial and venous blood vessel sites. Processing equipment of system 300 may generate two separate photoacoustic signals based on the acoustic pressure signal. Each photoacoustic signal may include a collection of points corresponding to particular travel times in the acoustic pressure signal, indicative of the respective arterial and venous sites. In some embodiments, an autocorrelation of an acoustic pressure signal may be used to identify two or more peaks in acoustic pressure, corresponding to pressure peaks from the arterial and venous sites.

As shown in FIG. 6, sensor units 640 and 650 are configured to monitor the external carotid artery and the external jugular vein, although any suitable artery and corresponding or nearby vein (e.g., radial, ulnar, or other artery and vein) may be monitored using the techniques disclosed herein.

It will be understood that although several illustrative sensor arrangements are shown in FIG. 6, any suitable number of sensor units may be used in accordance with the present disclosure. The use of multiple sensor units may increase signal to noise ratio, temporal resolution, spatial resolution, and/or a combination thereof. Any of the disclosed techniques may be used with any of the disclosed arrangements of FIG. 6, in accordance with the present disclosure.

Figure 7:
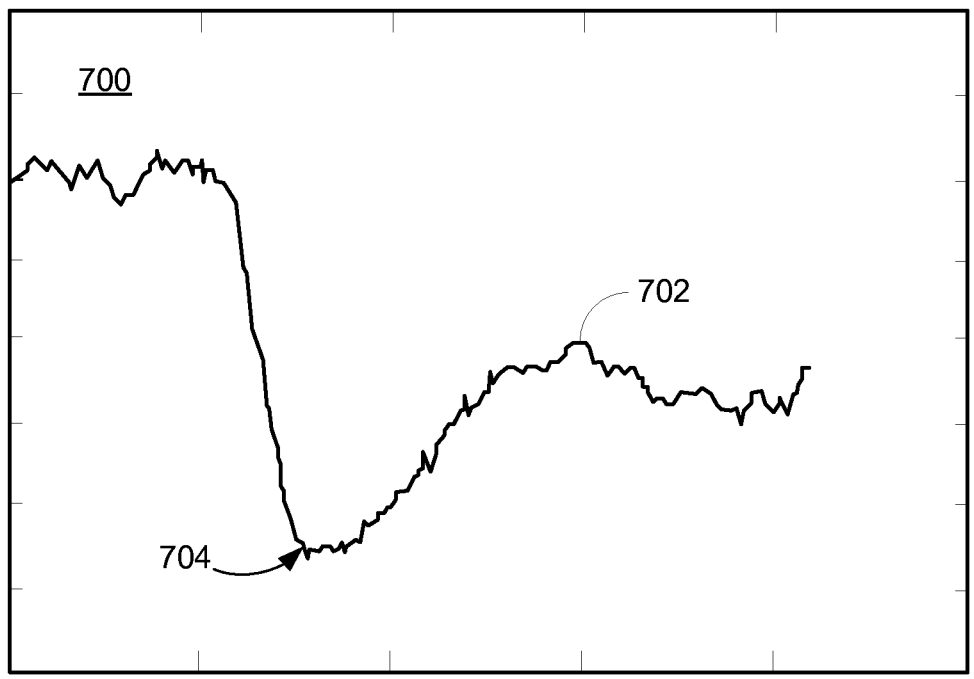
FIG. 7 shows an illustrative photoacoustic signal, including a response corresponding to an isotonic indicator, in accordance with some embodiments of the present disclosure.

FIG. 7 shows a plot 700 of an illustrative photoacoustic signal 702, including a response corresponding to an isotonic indicator (e.g., 0.9% w/v saline), in accordance with some embodiments of the present disclosure. A light source is used to provide a photonic signal to a first site of a circulatory system, causing a photoacoustic response of constituents in the circulating blood at that site. An acoustic detector is used to detect acoustic pressure signals caused by the photonic signal at the first site, and along with processing equipment, output a corresponding photoacoustic signal. An isotonic indicator is injected as a bolus dose into the circulating blood at a second site. As the bolus dose travels past the first site, the hemoglobin concentration at the first site temporarily decreases. Trough 704 indicates the dilatory effects of the bolus dose of isotonic indicator. The processing equipment outputs a reduced photoacoustic signal caused by the reduced hemoglobin concentration. The effect of the indicator may be detected as a trough in the photoacoustic signal corresponding to the passing of the bolus dose through the first site.

Figure 8:
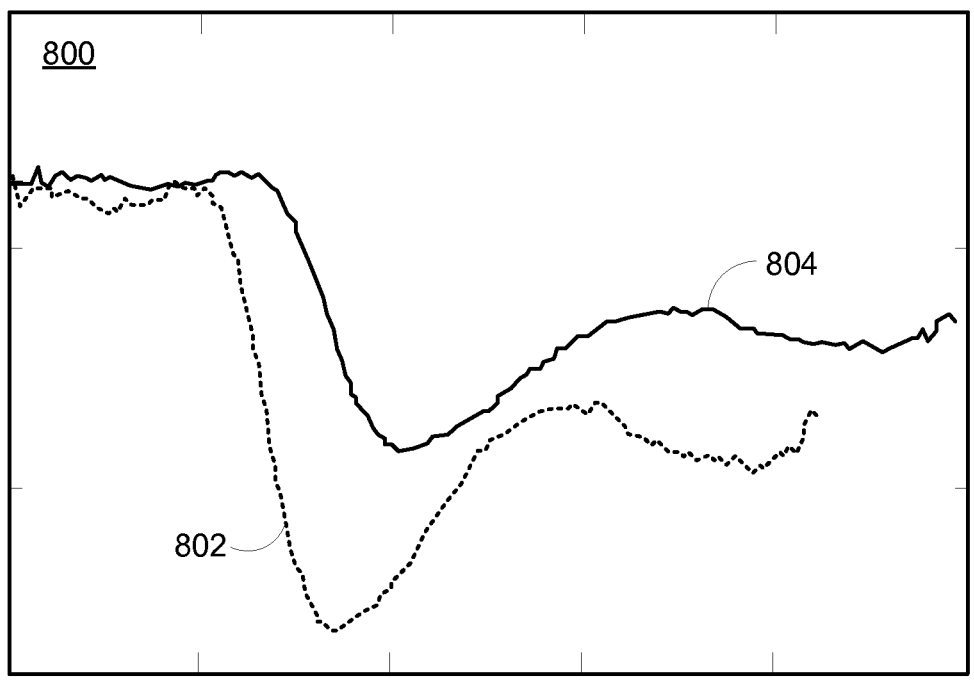
FIG. 8 shows a plot of two illustrative time series that correspond to photoacoustic signals, which include responses to an indicator passing through a carotid artery and a jugular vein of a subject, respectively, in accordance with some embodiments of the present disclosure.

FIG. 8 shows a plot 800 of two illustrative time series 802 and 804 that each correspond to photoacoustic signals, which include responses to an indicator passing through a carotid artery and a jugular vein of a subject, respectively, in accordance with some embodiments of the present disclosure. The abscissa of plot 800 is shown in units of time, while the ordinate of plot 800 is shown in arbitrary units proportional to acoustic pressure signal (e.g., in Volts). The bolus dose of the indicator may be first detected at the carotid artery site (shown by time series 802), as the bolus dose flows towards the subject's brain. As the indicator returns via the jugular vein (shown by time series 804), it may be detected again, at a later time relative to the first detection. Additionally, the shape of the response as detected in the jugular vein may differ from the shape of the response detected in the carotid artery. For example, diffusive and mixing effects may result in later time series 804 having a broader and shallower peak relative to earlier time series 802. In some embodiments, two photoacoustic signals may be monitored at sites other than the subject's neck. For example, a plot similar to plot 800 may be generated by monitoring a radial artery and a cephalic vein, a brachial artery and a basilica vein, any other suitable combination of an artery and corresponding vein, or any combination thereof. In some embodiments, the time delay and/or change in shape may be used to distinguish the indicator response of the arterial site from the indicator response of the venous site.

In some embodiments, one or more characteristics may be derived from one or both responses. For example, the flow rate of a particular indicator may be formulated as shown by:

$$\dot{V}C_i = \dot{N} \quad (14)$$

where $\dot{V}$ is the volumetric flow rate of blood (e.g., volume/time, assumed here to be constant in time), $C_i$ is the concentration of indicator i (e.g., mole/volume), and $\dot{N}$ is the molar flow rate of molecule i (e.g., mole/time). Defining the cardiac output CO to be equal to volumetric flow rate $\dot{V}$, and referencing time series 802, the following Eq. 15 may be derived by integrating both sides of Eq. 14 in time:

$$CO = \frac{N}{A} \quad (15)$$

where cardiac output CO is proportional to the total isotonic indicator amount introduced N (e.g., moles), and A is given by:

$$A = \int C_i dt \quad (16)$$

where A may be equivalent to the area 820 bounded by time series 802 and the steady tHb value. Under some circumstances, cardiac output may be equal to the ratio of isotonic indicator amount introduced and the area bounded by the time series and the steady tHb value, while in other circumstances the equality of Eqs. 15-16 may be replaced by the proportionality symbol $\alpha$ (e.g., to account for density differences). Area A is an illustrative example of a characteristic derived from a response to an indicator.

In a further example, EVLW may be determined based on isotonic and hypertonic indicators, as shown by Eq. 17:

$$EVLW = CO * \Delta\tau_{MT} \quad (17)$$

where CO is the cardiac output, and $\Delta\tau_{MT}$ is the mean transit time difference between the isotonic and hypotonic indicator dilution curves. The mean transit time of an indicator dilution curve may be based on any suitable reference point of the curve. The mean transit time for a dilution curve may be calculated using Eq. 18:

$$\tau_{MT} = \tau_0 + \frac{\int C_i * (t - \tau_0) dt}{\int C_i dt} \quad (18)$$

where $\tau_0$ is the time after introduction of the indicator when the indicator is detected at the PA monitoring site, and $C_i$ is the indicator concentration.

In a further example, a vascular permeability metric vp may be defined as:

$$vp = \tau_2 - \tau_1 \quad (19)$$

where $\tau_2$ is the time corresponding to a trough (i.e., minimum, occurring after a peak) of the response to the hypertonic indicator, and $\tau_1$ is the time where the responses to the isotonic and hypertonic indicators cross. In some circumstances, vascular permeability may provide an indication and/or measure of the possibility of a capillary leak and the possibility of fluid accumulating outside of the blood vessels.

In a further example, EVLW may be determined based on an osmotic response (e.g., the transfer of water and salt between the blood and lungs due to a chemical potential difference) of the subject using an isotonic and hypertonic indicator. EVLW may be determined using the following Eq. 20, for the hypertonic indicator:

$$EVLW = \frac{\Pi_b\left(\frac{\Delta n_3}{c} - \Delta EVLW_3\right)}{\Delta \Pi_{b,3}} \quad (20)$$

where $\Pi_b$ is the steady state osmolarity of the subject's blood (e.g., before introduction of the hypertonic indicator), $\Delta\Pi_{b,3}$ is the change in the osmolarity of subject's blood at time $\tau_3$, $\Delta n_3$ is the total amount of salt transferred from the subject's blood to the subject's lungs at time $T_3$, C is the concentration of solutes in the EVLW, and $\Delta EVLW_3$ is the total change in extravascular lung water at time $\tau_3$. The time $\tau_3$ is the time, referenced to zero at the beginning of the response, when the EVLW and blood have the same osmotic pressure for the hypertonic indicator.

In some embodiments, a thermo-dilution indicator may be introduced to the subject's circulatory system at a suitable location. For example, in some embodiments, a saline solution having a temperature less than that of a subject's blood may be introduced, and one or more dilution curves may be measured at one or more respective locations in the subject's vasculature. The Grüneisen parameter of the subject's blood may depend on temperature linearly according to:

$$\Gamma = mT + b \quad (21)$$

where m is a slope and b is an intercept. Accordingly, Eq. 1 may be rewritten as follows:

$$p(z,T) = \Gamma(T)\mu_a\phi(z) \quad (22)$$

Showing that as the temperature at the photoacoustic monitoring site changes, the acoustic pressure signal and a photoacoustic signal derived thereof may change accordingly. Introduction of thermo-dilution indicator may be used to determine cardiac output, ITCV, PCV, and/or GEDV, for example.

In some embodiments, cardiac output CO may be calculated using:

$$CO = K\frac{(T_{b,0} - T_{i,0})V_i}{\int (T_{b,0} - T_b(t))dt} \quad (23)$$

where K is a proportionality constant (e.g., including the effects of specific gravity and heat capacity of blood and/or the indicator), $T_{b,0}$ is the initial blood temperature at the time and site of injection, $T_{i,0}$ is the initial indicator temperature, $V_i$ is the volume of injected indicator, and $T_b(t)$ is the blood temperature at time t, as measured using the photoacoustic technique. Note that the moles of injected indicator may be used rather than $V_i$ in some cases, with a suitable adjustment of the proportionality constant K to include the indicator concentration (e.g., mole/volume).

In some embodiments, ITCV may be calculated using:

$$ITCV = CO * \tau_{MT} \quad (24)$$

where CO is the cardiac output, and $\tau_{MT}$ is the mean transit time of the thermo-dilution curve. The mean transit time for a thermo-dilution indicator may be calculated using:

$$\tau_{MT} = \tau_0 + \frac{\int (T_{b,0} - T_b(t)) * (t - \tau_0)dt}{\int (T_{b,0} - T_b(t))dt} \quad (25)$$

where $\tau_0$ is the time after introduction of the indicator when the indicator is detected at the PA monitoring site, and $(T_{b,0} - T_b(t))$ is the difference in initial and instantaneous blood temperature of the thermo-dilution curve. In some embodiments, in which a thermo-dilution indicator may be used, a circulatory volume may be equivalent to a thermal volume.

In some embodiments, PCV may be calculated using:

$$PCV = CO * \tau_{DS} \quad (26)$$

where CO is the cardiac output, and $\tau_{DS}$ is the downslope time of the thermo-dilution curve. In some embodiments, the downslope time may be determined as the time interval of the linear decay of the indicator response (e.g., downslope of a peak), from about 80% of the peak value to about 20% of the peak value. In some circumstances, downslope time may provide an indication and/or measure of the washout of the indicator, which may depend on the volume which the indictor dilutes.

In some embodiments, GEDV may be calculated using:

$$GEDV = ITCV - PCV \quad (27)$$

which may be indicative of the blood volume included in the ITCV.

In some embodiments, EVLW may be calculated using:

$$EVLW = ITCV - ITBV \quad (28)$$

where ITBV may be calculated from GEDV, which may be calculated using Eq. 27. For example, ITBV may be directly proportional to GEDV, with a proportionality constant of order one (e.g., a constant of 1.25).

In some embodiments, more than one thermo-dilution indicator may be introduced to a subject. For example, two thermo-dilution indicators, at two different temperatures, may be introduced to the subject. Differences in the resulting dilution curves may provide information regarding hemo-dilution, thermo-dilution, or differences thereof.

In some embodiments, both a thermo-dilution indicator and a hemo-dilution indicator may be introduced to the subject's circulatory system at suitable locations and times. For example, in some embodiments, a saline solution having a temperature less than that of a subject's blood may be introduced, and a dye indicator such as indocyanine green dye may be introduced. Accordingly, two or more dilution curves may be measured at one or more locations in the subject's vasculature, indicative of the hemo-dilution and thermo-dilution indicators. Any of the properties that may be calculated using Eqs. 21-27 may be calculated using the thermo-dilution indicator. In some embodiments, ITBV may be calculated using the hemo-dilution curve, as shown by:

$$ITBV = -CO^* \tau_{MT} \quad (29)$$

where CO is the cardiac output (e.g., calculated using Eq. 15 or 23), and $\tau_{MT}$ is the mean transit time of the hemo-dilution curve (e.g., calculated using Eq. 18).

In some embodiments, EVLW may be calculated from the thermo-dilution curve and hemo-dilution curve using:

$$EVLW = ITCV - ITBV \quad (30)$$

wherein ITCV may be calculated from the thermo-dilution curve (e.g., using Eq. 24), and ITBV may be calculated from the hemo-dilution curve (e.g., using Eq. 29).

Figure 9:
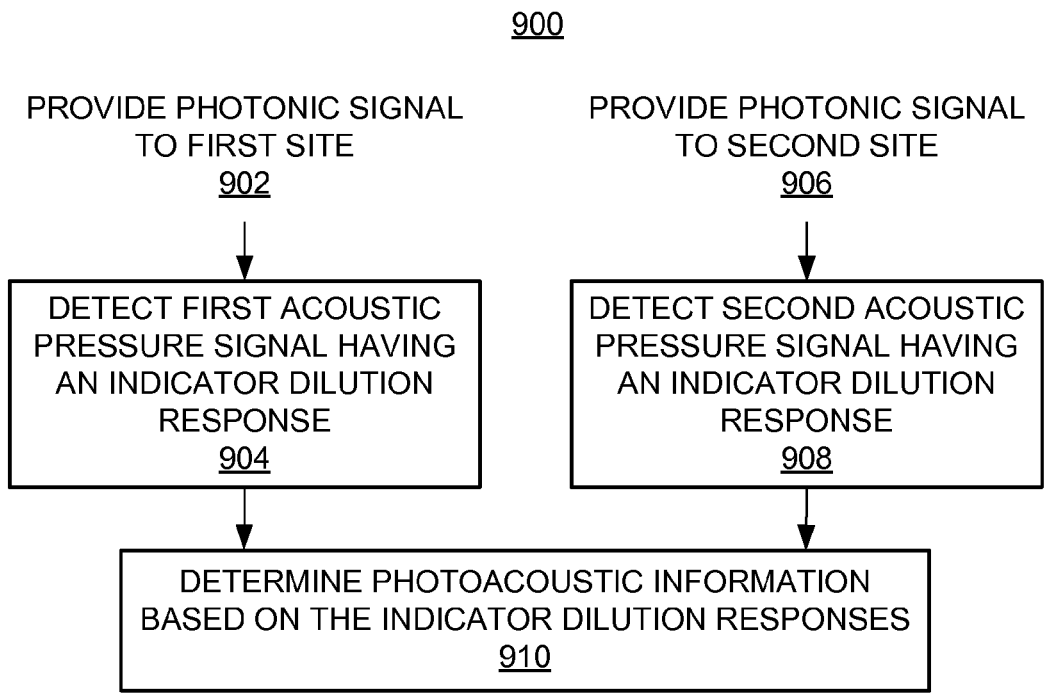
FIG. 9 is a flow diagram of illustrative steps for determining a physiological parameter based on two detected acoustic pressure signals, in accordance with some embodiments of the present disclosure.
Figure 10:
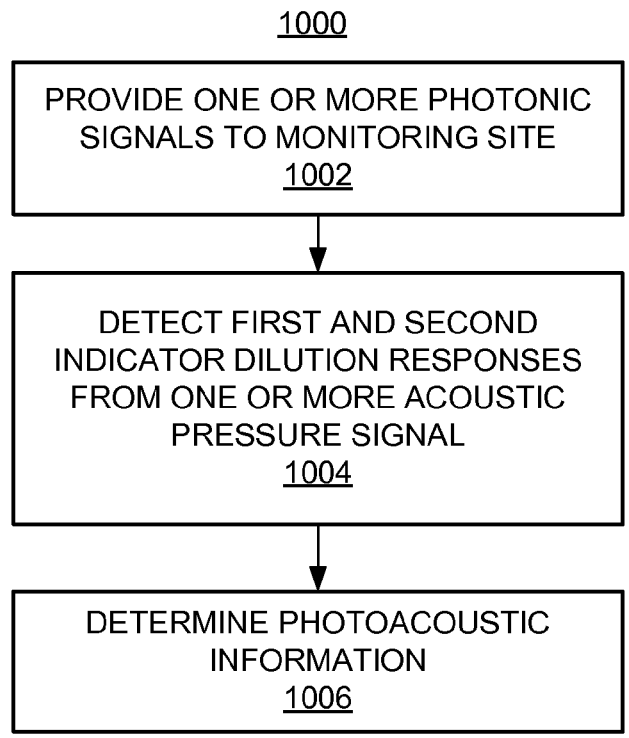
FIG. 10 is a flow diagram of illustrative steps for determining a physiological parameter based on two indicator dilution responses, in accordance with some embodiments of the present disclosure.

Any of the thermal-dilution and hemo-dilution techniques, using one or more indicators and one or more sensor units, may be used alone or in combination with other techniques. FIGS. 9 and 10 include flowcharts of illustrative steps for implementing the aforementioned techniques. The illustrative steps of flow diagrams 900 and 1000 may be implemented using any of the systems (e.g., those systems shown and/or discussed in the context of FIGS. 1-3) and/or arrangements (e.g., those arrangements shown and/or discussed in the context of FIG. 6) of the present disclosure.

FIG. 9 is a flow diagram 900 of illustrative steps for determining a physiological parameter based on two detected acoustic pressure signals, in accordance with some embodiments of the present disclosure.

Step 902 may include a suitable light source (e.g., light source 16 of system 10) of system 300 providing a photonic signal to a first site of a subject. Step 906 may include a suitable light source, the same or different from the light source of step 902, providing a photonic signal to a second site of a subject. For example, the photonic signal provided to the first and second site may be the same photonic signal, provided by the same light source. In a further example, a first light source may provide a photonic signal to the first site, and a second light source may provide a photonic signal to the second site. The light source(s) may be a pulsed, continuous wave, any other suitable type of light source, or any combination thereof. In some embodiments, modulator 44 may be used to modulate the photonic signal of the light source(s). In some embodiments, the photonic signal(s) may be focused or otherwise spatially modulated. For example, a photonic signal may be focused on or near a blood vessel, which may contain blood that absorbs at least some of the photonic signal, causing a relatively stronger photoacoustic response and accordingly a stronger photoacoustic signal than surrounding tissue.

Step 904 may include system 300 detecting a first acoustic pressure signal, based on the photonic signal of step 902, having an indicator response. In some embodiments, an acoustic detector such as, for example, an ultrasound detector of system 300 may detect the first acoustic pressure signal. Step 908 may include system 300 detecting a second acoustic pressure signal, using the same acoustic detector or different acoustic detector as step 904, having an indicator response. The acoustic detector(s) may output an electrical signal (i.e., a photoacoustic signal) to suitable processing equipment of system 300. The acoustic pressure signal(s) may be detected as a time series (e.g., in the time domain or sample number domain), and processed as a time series, as a spectral series (e.g., in the frequency domain), any other suitable series, or any combination thereof. In some embodiments, pre-processor 320 may pre-process a detected acoustic pressure signal. For example, pre-processor 320 may perform filtering, amplifying, de-multiplexing, de-modulating, sampling, smoothing, any other suitable pre-processing, or any combination thereof. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. The photoacoustic signal(s) may include a hemo-dilution and/or thermo-dilution response characterized by a temporal peak or trough in concentration, temperature, any other suitable property of the monitoring site, any changes thereof, or any combination thereof. In some embodiments, processor 312 may use a peak finding technique to locate a peak and/or trough in a photoacoustic signal. For example, processor 312 may locate a maximum or minimum in the photoacoustic signal, locate a zero in the first derivative of the photoacoustic signal, perform any other suitable peak finding technique, or any combination thereof. The peak finding technique may operate on only a subset of the photoacoustic signal. For example, the peak finding algorithm may only start looking for a peak and/or trough after a predetermined time or sample number from the introduction of the indicator.

Step 910 may include system 300 determining one or more physiological parameters of the subject based at least in part on the indicator dilution response detected at steps 904 and/or 908. Physiological parameters may include hemoglobin, blood oxygen saturation, CO, ITBV, ITCV, GEDV, PCV, EVLW, any other suitable hemodynamic parameters, any other suitable physiological parameters, any physiological modulations thereof, or any combination thereof. In some embodiments, step 910 may include processor 312 determining one or more characteristics based at least in part on the indicator dilution response. Processor 312 may determine characteristics such as particular values of the photoacoustic signal or values of a signal derived thereof (e.g., a tHb value), areas under or between signals (e.g., integrals), temporal values or differences (e.g., as shown by Eqs. 18, 19, and 25), any other suitable characteristics, or any combination thereof. For example, processor 312 may calculate one or more physiological parameters using any or all of Eqs. 14-20 and 23-30, based on one or more indicator dilution responses.

In some embodiments, in which the first site is substantially coincident with the second site, step 910 may include combining, comparing, or otherwise considering both the first and second photoacoustic signals. For example, system 300 may average the first and second photoacoustic signals output at steps 904 and 908, respectively, and then determine one or more physiological parameters using any or all of Eqs. 14-20 and 23-30. In a further example, system 300 may determine one or more physiological parameters using any or all of Eqs. 14-20 and 23-30 for each of the first and second photoacoustic signals of steps 904 and 908, respectively, and then average the resulting determined physiological parameters. The average may be an ensemble average, a weighted ensemble average, any other suitable average, or any combination thereof. In a further example, system 300 may compare the first and second photoacoustic signals outputted at steps 904 and 908, respectively, and determine one or more physiological parameters based on the photoacoustic signal having the relatively largest magnitude of indicator response (e.g., deepest trough or highest peak relative to a baseline). In a further example, system 300 may compare the first and second photoacoustic signals outputted at steps 904 and 908, respectively, and compute a difference between the photoacoustic signals. If the difference is larger than a threshold, system 300 may disregard one or both photoacoustic signals, and need not determine a physiological parameter from the disregarded signal(s). In a further example, distinct photonic signals provided to the monitoring site (i.e., coincident first and second sites) by distinct light sources may be out of phase by a half period. System 300 may combine the first and second photoacoustic signals outputted at steps 904 and 908, respectively, to create a single time series with a sample rate effectively twice that achieved by using either single detector. In a further example, distinct photonic signals provided to the monitoring site (i.e., coincident first and second sites) by distinct light sources may be in phase. The use of in-phase light sources may increase the signal to noise ratio, the photonic signal available to cause a photoacoustic response, or both.

In some embodiments, three or more sensors may be included at substantially the same site. In some embodiments, processor 312 may perform a cross-correlation to determine a time delay between features of the photoacoustic signals of multiple sensors. After applying a suitable time shift to account for the time delay, the multiple signals may then be averaged, summed, and/or compared. For example, the photoacoustic signal of the sensor unit differing most (e.g., in shape, value, or other property) from the signals of the other sensors (e.g., based on a difference, or statistical calculation) may be discarded, and the remaining signals may be further processed. In a further example, each photoacoustic signal or features therein may include one or more frequencies. If components of the signal are at frequencies outside of an expected range of interest, the signal may be determined to be relatively noisier. For example, the signal energy above and below 1 Hz may be determined (may need to look at raw samples at components above 1 Hz), and compared to determine the level of noise in a signal. In a further example, skewness of a dilution curve derived from an acoustic pressure signal may be determined and compared with a predefined value (e.g., more skew may be expected nearer the heart, with a steeper initial portion of the response and more gradual return of the signal to a steady condition).

In some embodiments, in which the first site and the second site are located in the same blood vessel but the second site is distal to the first site, step 910 may include comparing both the first and second detected acoustic pressure signals. For example, the first and second sites may be along a radial artery of a subject, and a thermal indicator may be introduced to the subject. System 300 may determine one or more differences in the shape of the indicator responses (e.g., peak/trough heights, peak/trough widths, integrated area of peaks/trough, peak/trough skewness) detected at the first and second sites. System 300 may determine one or more physiological parameters based on the one or more differences by using a correlation, equation, look-up table, any other suitable reference, or any combination thereof. In a further example, a thermodilution indicator may be introduced to the subject. The detected indicator responses at the first and second sites may have relatively different shapes. While the blood to saline ratio may be expected to be constant at the first and second sites, the temperature gradient may be reduced at the distal sensor due to the increased time for heat transfer. Accordingly the effects of hemo-dilution and thermo-dilution may be distinguished by the use of two or more monitoring sites.

In some embodiments, in which the first site and the second site are located at similar left and right sites of corresponding left and right blood vessels of a subject, step 910 may include combining, comparing, or otherwise considering both the first and second photoacoustic signals. For example, system 300 may average the first and second photoacoustic signals output at steps 904 and 908, respectively, and then determine one or more physiological parameters using any or all of Eqs. 14-20 and 23-30. In a further example, system 300 may determine one or more physiological parameters using any or all of Eqs. 14-20 and 23-30 for each of the first and second photoacoustic signals of steps 904 and 908, respectively, and then average the resulting determined physiological parameters. In a further example, system 300 may compare the first and second photoacoustic signals outputted at steps 904 and 908, respectively, and compute a difference between the photoacoustic signals. The difference may be computed in photoacoustic signal amplitudes, time lags of one or more features of the photoacoustic signals, signal to noise ratios of the photoacoustic signals, any other photoacoustic signal property, or any combination thereof. If the difference is larger than a threshold, system 300 may disregard one or both photoacoustic signals, and need not determine a physiological parameter from the disregarded signal(s).

In some embodiments, two or more indicators may be used to determine a physiological parameter, using one or more sensors at a monitoring site. One or more suitable light sources (e.g., one or more of light source 16 of system 10) of system 300 providing one or more photonic signals to a subject, at the monitoring site. The light source(s) may be a pulsed, continuous wave, modulated, any other suitable type of light source, or any combination thereof. In some embodiments, the photonic signal may be provided at two particular times to monitor respective first and second responses. For example, the photonic signal may be provided in response to the introduction of an indicator, at a suitable time to monitor the response at the monitoring site of the subject. A first indicator may be provided at a first time, having a first temperature, and a second indicator may be provided at a second time, having a second temperature, to the subject. In some embodiments, a bolus dose of each indicator may be injected using a hypodermic needle, for example, inserted into a blood vessel of the subject. The bolus doses may include, for example, a volume on the order of ten milliliters. The second time may be before or after the first time (i.e., the introduction of the indicators may be in any suitable order). In some embodiments, one of the two indicators may be introduced at substantially the same temperature of the subject at the introduction site. In some such embodiments, the bolus dose of the other indicator may be introduced at a temperature different from the temperature of the subject at the introduction site (e.g., the bolus dose may be relatively warmer or cooler). One or more acoustic detectors of system 300 may detect an acoustic pressure signal having a first and a second response, corresponding to the first and second indicators. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. The photoacoustic signal may include a first and a second response, which may be Nemo-dilution and/or thermo-dilution responses, depending on the temperature of the indicator when injected. The responses may be characterized by a temporal peak or trough in concentration, temperature, any other suitable property of the monitoring site, any changes thereof, or any combination thereof. System 300 may determine one or more physiological parameters of the subject based at least in part on the first and second responses detected at step 904. In some embodiments, using two indicators of different temperature may aid in distinguishing the effects of Nemo-dilution and thermo-dilution.

FIG. 10 is a flow diagram 1000 of illustrative steps for determining a physiological parameter based on a first and second indicator dilution responses, in accordance with some embodiments of the present disclosure.

Step 1002 may include one or more suitable light sources (e.g., light source 16 of system 10) of system 300 providing one or more photonic signal to a subject, at a monitoring site. The light source(s) may be pulsed, continuous wave, any other suitable type of light source, or any combination thereof. In some embodiments, modulator 44 may be used to modulate the photonic signal of a light source. In some embodiments, the photonic signal may be focused or otherwise spatially modulated. In some embodiments, the monitoring site may include a region, which may include an arterial site and a corresponding venous site, which may receive the same or different photonic signals from the one or more light sources.

Step 1004 may include system 300 detecting an acoustic pressure signal having a first and a second indicator dilution response, using one or more acoustic detectors. The one or more acoustic detectors may output an electrical signal to suitable processing equipment of system 300. In some embodiments, processor 312 and/or pre-processor 320 may generate a photoacoustic signal from a time series of peak values in a detected acoustic pressure signal, occurring at a particular time lag indicative of a spatial location, resulting from the photoacoustic response to the photonic signal. The first and second responses may correspond to the indicator passing through an artery and then a vein, respectively, at the first site. As a bolus does passes through the artery at the monitoring site, a photoacoustic signal derived from the acoustic pressure signal detected by one or more sensor units may exhibit an indicator response. After traveling through the capillaries and/or tissue of the subject, the bolus dose may pass through a vein at the monitoring site. The one or more sensor units may detect an acoustic pressure signal, and a photoacoustic signal derived thereof may exhibit another indicator response, although shifted in time relative to the response at the arterial site. In some embodiments, using more than one detector, processor 312 may use the time shift, which may be calculated using a cross-correlation of the two photoacoustic signals, to distinguish the arterial response form the relatively later venous response. In some embodiments, using a single detector, processor 312 may use the time shift, which may be calculated using an autocorrelation of the photoacoustic signal, to distinguish the arterial response from the relatively later venous response. In some embodiments, the first and second responses may be detected as peaks or troughs in the photoacoustic signal, distinguishable from a baseline value or curve in the photoacoustic signal. In some embodiments, two acoustic detectors may be used, one monitoring an arterial site and the other monitoring a nearby corresponding venous site. In some such embodiments, which may use the same or different light sources, a cross-correlation may be used to determine the time shift. In some embodiments, a single acoustic detector may be used, which may detect both the first and second indicator dilution responses. The detected acoustic pressure signal may include responses at the arterial and venous sites shifted in time due to the travel times of the acoustic pressure waves to the detector. In some such embodiments, processing equipment of system 300 may separate the first and second responses as separate photoacoustic signals, based on the travel time difference.

Step 1006 may include system 300 determining photoacoustic information, which may include one or more physiological parameters of the subject, based at least in part on first and second indicator responses of step 1004. Physiological parameters may include hemoglobin, blood oxygen saturation, CO, ITBV, ITCV, GEDV, PCV, EVLW, any other suitable hemodynamic parameters, any other suitable physiological parameters, any physiological modulations thereof, or any combination thereof. For example, processor 312 may calculate one or more physiological parameters based on suitable characteristics using any or all of Eqs. 14-30. In some embodiments, step 1006 may include system 300 analyzing the first indicator dilution response and the second dilution response. The analysis may include determining a time difference between the first indicator dilution response and the second indicator dilution response, determining a shape difference between the first indicator dilution response and the second indicator dilution response, distinguishing the first indicator dilution response from the second indicator dilution response, any other suitable analysis, or any combination thereof. In some embodiments, step 1006 may include distinguishing an acoustic pressure signal, or component thereof, arising from an artery from an acoustic pressure signal, or component thereof, arising from a vein. For example, the acoustic detector may distinguish the arterial response from the venous response by determining which occurs first in time (e.g., the indicator passes through the artery before the corresponding vein). Accordingly, in some embodiments, system 300 may determine one or more physiological parameters based on one of the indicator responses (e.g., based on either the arterial or venous response).

In the foregoing flowcharts, an acoustic pressure signal having one or more indicator dilution responses is detected. In some embodiments, the system (e.g., system 300) may continuously detect the acoustic pressure signal and continuously analyze a derived photoacoustic signal to identify the one or more indicator responses. In some embodiments, the system may only detect and analyze the acoustic pressure signal in response to a user input. For example, the user may press a key on the monitor shortly before the one or more indicators are injected. In some embodiments, the system may be communicatively coupled to the injection apparatus and therefore may automatically know when the one or more indicators are injected and when to detect the acoustic pressure signal. For example, the injection apparatus may transmit a signal to the system each time there is an injection. As another example, the system may control the injection apparatus and instruct the injection apparatus when to perform an injection.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for determining a physiological parameter of a subject, the method comprising:
    detecting a first acoustic pressure signal and a second acoustic pressure signal using one or more acoustic detectors, wherein the first acoustic pressure signal and the second acoustic pressure signal are caused by absorption of at least some of one or more photonic signals by one or more constituents in a first blood vessel and in a second blood vessel, respectively, and wherein the first acoustic pressure signal and the second acoustic pressure signal comprise dilution responses corresponding to an indicator;
    deriving a first photoacoustic signal from the first acoustic pressure signal and a second photoacoustic signal from the second acoustic pressure signal;
    comparing the first photoacoustic signal to the second photoacoustic signal to determine a shape difference or a time difference between the first and second photoacoustic signals;
    determining whether the first blood vessel or the second blood vessel is an artery or a vein based at least in part on the shape difference or the time difference;
    selecting the first photoacoustic signal or the second photoacoustic signal based at least in part on the determination of whether the first blood vessel or the second blood vessel is the artery or the vein; and
    determining the physiological parameter based at least in part on the selected first photoacoustic signal or the second photoacoustic signal.

2. The method of claim 1, wherein determining the physiological parameter is based at least in part on the time difference between the dilution response of the first acoustic pressure signal and the dilution response of the second acoustic pressure signal.

3. The method of claim 2, wherein the first blood vessel and the second blood vessel comprise respective vessels of at least one of a carotid artery and a jugular vein, a radial artery and a cephalic vein, and an ulnar artery and an ulnar vein.

4. The method of claim 2, wherein the physiological parameter is a flow rate of blood through an organ located between the first vessel and the second vessel.

5. The method of claim 1, wherein a first photonic signal of the one or more photonic signals is out of phase relative to a second photonic signal of the one or more photonic signals.

6. The method of claim 1, wherein the physiological parameter is one of cardiac output, intrathoracic blood volume, intrathoracic circulatory volume, global end-diastolic volume, pulmonary circulatory volume, and extravascular lung water.

7. The method of claim 1, wherein the first acoustic pressure signal comprises a first response to a first thermo-dilution indicator and a second response to a second thermo-dilution indicator, and wherein the second acoustic pressure signal comprises a first response to the first thermo-dilution indicator and a second response to the second thermo-dilution indicator, and wherein the first and the second thermo-dilution indicators are introduced to the subject at different temperatures.

8. The method of claim 1, further comprising determining a value indicative of signal confidence based on at least one of the first acoustic pressure signal and the second acoustic pressure signal, and wherein the determining the physiological parameter is further based on the value indicative of signal confidence.

9. The method of claim 1, wherein determining the time difference or the shape difference comprises cross-correlating the first and the second photoacoustic signals.

10. The method of claim 1, wherein the shape difference is based at least in part on a peak or trough height, peak or trough width, an integrated area of peak or trough, or a peak or trough skewness.

11. The method of claim 1, wherein the constituent is hemoglobin.

12. A system for determining a physiological parameter of a subject, the system comprising:
    one or more light sources configured to provide one or more photonic signals to one or more monitoring sites of the subject;
    one or more acoustic detectors configured to detect a first acoustic pressure signal and a second acoustic pressure signal from the one or more monitoring sites, wherein the first acoustic pressure signal and the second acoustic pressure signal are caused by the absorption of at least some of the one or more photonic signals by one or more constituents in a first blood vessel and a second blood vessel, respectively, and wherein the first acoustic pressure signal and the second acoustic pressure signal comprise a responses corresponding to an indicator; and
    processing equipment configured to:
        derive a first photoacoustic signal from the first acoustic pressure signal and a second photoacoustic signal from the second acoustic pressure signal;
        compare the first photoacoustic signal to the second photoacoustic signal to determine a shape difference or a time difference between the first and second photoacoustic signals;
        determine whether the first blood vessel or the second blood vessel is an artery or a vein based at least in part on the shape difference or the time difference;
        select the first photoacoustic signal or the second photoacoustic signal based at least in part on the determination of whether the first blood vessel or the second blood vessel is the artery or the vein; and
        determine the physiological parameter based at least in part on the selected first photoacoustic signal or the second photoacoustic signal.

13. The system of claim 12, wherein the processing equipment is configured to determine the physiological parameter based at least in part on the time difference between the first response of the first acoustic pressure signal and the second response of the second acoustic pressure signal.

14. The system of claim 13, wherein the first blood vessel and the second blood vessel comprise respective vessels of at least one of a carotid artery and a jugular vein, a radial artery and a cephalic vein, and an ulnar artery and an ulnar vein.

15. The system of claim 12, wherein a first photonic signal of the one or more photonic signals provided to the one or more monitoring sites is out of phase relative to a second photonic signal of the one or more photonic signals provided to the one or more monitoring sites.

16. The system of claim 12, wherein the processing equipment is further configured to determine one of cardiac output, intrathoracic blood volume, intrathoracic circulatory volume, global end-diastolic volume, pulmonary circulatory volume, and extravascular lung water.

17. The system of claim 12, wherein the first acoustic pressure signal comprises a first response to a first thermo-dilution indicator and a second response to a second thermo-dilution indicator, and wherein the second acoustic pressure signal comprises a first response to the first thermo-dilution indicator a second response to the second thermo-dilution indicator, and wherein the first and the second thermo-dilution indicators are introduced to the subject at different temperatures.

18. The system of claim 12, wherein the processing equipment is further configured to determine a value indicative of signal confidence based on at least one of the first photoacoustic signal and the second photoacoustic signal, and wherein the determining the physiological parameter is further based on the value indicative of signal confidence.

19. The system of claim 12, comprising at least one sensor unit having a sensor body comprising at least one light source and at least one acoustic detector.

20. The system of claim 19, wherein the sensor body comprises multiple acoustic detectors.

21. The system of claim 19, wherein the sensor unit comprises an encoder storing information related to whether the at least one light source is configured to emit pulsed or continuous wave light.

* * * * *